(12) United States Patent
Shuffler et al.

(10) Patent No.: US 11,759,260 B2
(45) Date of Patent: *Sep. 19, 2023

(54) STEERABLE AND CONTROLLABLE MEDICAL LASER FIBERS

(71) Applicants: Samuel H. Shuffler, Lafayette, LA (US); Mark G. Fontenot, Lafayette, LA (US)

(72) Inventors: Samuel H. Shuffler, Lafayette, LA (US); Mark G. Fontenot, Lafayette, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/669,915

(22) Filed: Oct. 31, 2019

(65) Prior Publication Data
US 2020/0305975 A1 Oct. 1, 2020

Related U.S. Application Data

(63) Continuation of application No. 13/772,025, filed on Feb. 20, 2013, now Pat. No. 10,478,251.

(51) Int. Cl.
A61B 18/24 (2006.01)
A61M 25/01 (2006.01)
A61M 25/10 (2013.01)
A61B 18/22 (2006.01)

(52) U.S. Cl.
CPC ......... *A61B 18/24* (2013.01); *A61M 25/0136* (2013.01); *A61M 25/0147* (2013.01); *A61B 2018/2238* (2013.01); *A61M 25/0108* (2013.01); *A61M 25/10* (2013.01); *A61M 2025/015* (2013.01); *Y10T 29/49002* (2015.01)

(58) Field of Classification Search
CPC ............ A61B 18/24; A61B 2018/2238; A61B 2018/00505; A61B 2018/00517; A61B 2017/22045; A61M 25/0136; A61M 25/0147; A61M 25/10; A61M 2025/015; A61M 25/0108; A61M 2210/1078; A61M 2210/1085; Y10T 29/49002; A61F 2/042
See application file for complete search history.

(56) References Cited

U.S. PATENT DOCUMENTS

| 4,586,923 | A | * | 5/1986 | Gould | A61M 25/09033 600/434 |
| 4,846,171 | A | * | 7/1989 | Kauphusman | A61B 18/245 606/15 |
| 5,306,244 | A | * | 4/1994 | Shiber | A61B 8/12 600/585 |
| 5,372,587 | A | * | 12/1994 | Hammerslag | A61M 25/0053 600/585 |
| 5,431,168 | A | * | 7/1995 | Webster, Jr. | A61B 18/1492 600/435 |

(Continued)

*Primary Examiner* — Joseph M Dietrich
*Assistant Examiner* — Michael T. Holtzclaw
(74) *Attorney, Agent, or Firm* — BAKER DONELSON PC

(57) ABSTRACT

A device includes a catheter section comprising a flexible joint region disposed between a distal end and a proximal end. The device includes a laser fiber disposed within the catheter section. The laser fiber emits laser light at a fiber distal end. The device includes a wire comprising a distal end coupled to the catheter section. The wire is configured to move the distal end of the catheter section from a first position to a second position about the flexible joint region.

21 Claims, 20 Drawing Sheets

(56) References Cited

U.S. PATENT DOCUMENTS

| | | | | |
|---|---|---|---|---|
| 5,470,330 A | * | 11/1995 | Goldenberg | A61B 1/00165 606/10 |
| 5,499,973 A | * | 3/1996 | Saab | A61M 25/0054 600/435 |
| 5,514,128 A | * | 5/1996 | Hillsman | A61B 18/245 600/585 |
| 5,533,987 A | * | 7/1996 | Pray | A61M 25/0054 604/264 |
| 5,545,200 A | * | 8/1996 | West | A61B 18/1492 606/29 |
| 5,843,050 A | * | 12/1998 | Jones | A61M 25/0075 604/525 |
| 2001/0009986 A1 | * | 7/2001 | Ponzi | A61B 18/24 604/95.04 |
| 2003/0199860 A1 | * | 10/2003 | Loeb | A61B 18/24 606/17 |
| 2005/0272975 A1 | * | 12/2005 | McWeeney | A61M 25/0068 600/113 |
| 2006/0252993 A1 | * | 11/2006 | Freed | A61M 25/0147 600/146 |
| 2017/0189113 A1 | * | 7/2017 | Urbanski | A61M 5/007 |

* cited by examiner

| Parameter | Gyrun ACMI | | | Olympus | Karl Storz | Richard Wolf | | |
|---|---|---|---|---|---|---|---|---|
| | DUR-D | DUR-8 | DUR-8 Elite | URF-P5 | Flex-X2 | 7330 (0.072) | 7325 (0.172) | 7325 (0.071) |
| Tip diameter (Fr) | 8.7 | 6.75 | 6.75 | 5.3 | 7.5 | | 6.8 | 6.0 |
| Shaft diameter (Fr) | 9.3 | 8.6 | 8.6 | 8.4 | 8.4 | 9.0 | 7.5 | 8.8 |
| Working length (cm) | 65 | 65 | 65 | 70 | 70 | 70 | 70 | 68 |
| Channel size (Fr) | 3.6 | 3.6 | 3.6 | 3.6 | 3.6 | 4.5 | 3.6 | 3.6 |
| Active deflection up (°) | 250 | 175 | 175 | 180 | 270 | 130 | 130 | 270 |
| Active deflection down (°) | 250 | 185 | 185 | 275 | 270 | 160 | 160 | 270 |
| Active secondary deflection (°) | 0 | 0 | 165 | 0 | 0 | 0 | 0 | 0 |
| Angle of view (°) | 9 | 12 | 12 | 0 | 6 | 0 | 0 | 0 |
| Field of view (°) | 80 | 80 (±5) | 80 (±5) | 90 | 90 | 65 | 65 | 65 |
| Depth of field (mm) | | 2 to 40 | 2 to 40 | 2 to 50 | 2 to 50 | 2 to 40 | 2 to 40 | 2 to 40 |
| Magnification | Zoom | 30X | 30X | 52X | 40X | 50X | 50X | 50X |

FIGURE 5

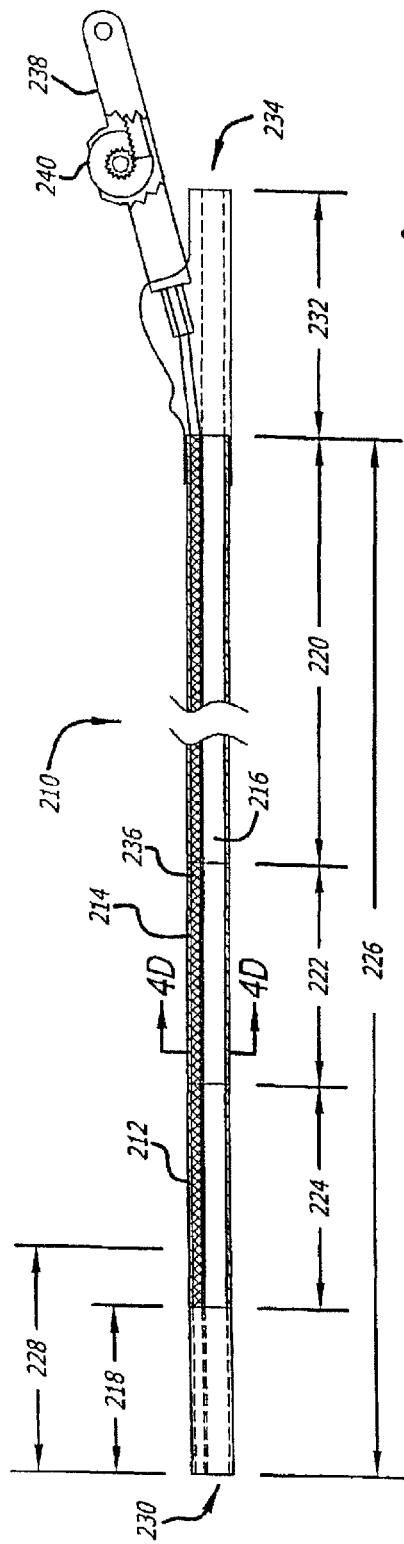
FIG. 9A
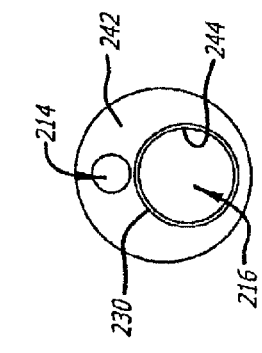
FIG. 9B
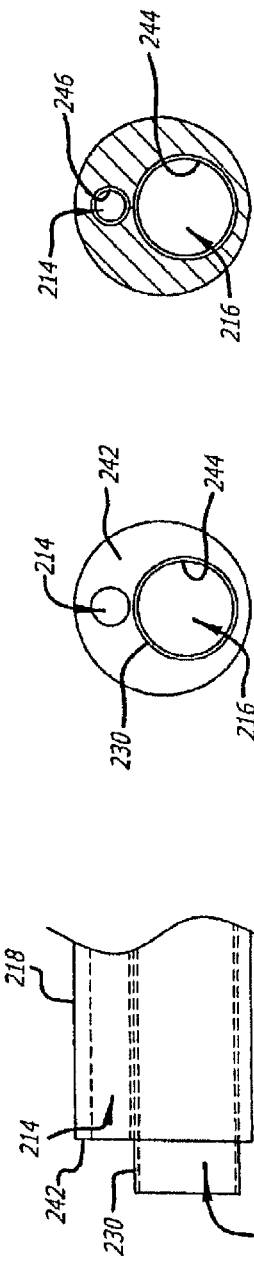
FIG. 9C
FIG. 9D

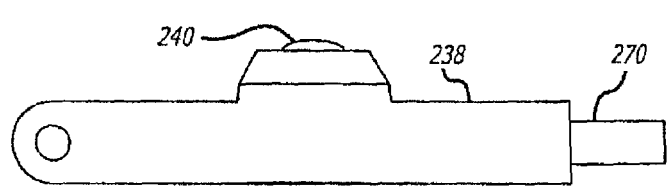
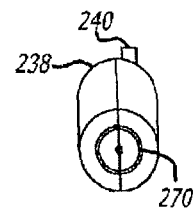
FIG. 12A          FIG. 12B
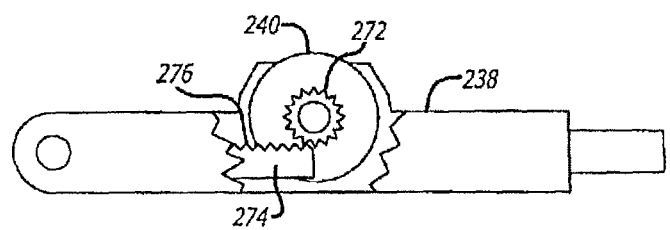
FIG. 12C
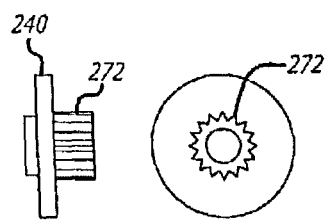
FIG. 12D
FIG. 12E

STEERABLE AND CONTROLLABLE MEDICAL LASER FIBERS

RELATED APPLICATION

This application claims the benefit of U.S. Patent Application No. 61/600,981, filed Feb. 20, 2012.

This application is a continuation in part application of U.S. patent application Ser. No. 11/641,490, filed Dec. 19, 2006.

This application is a continuation in part application of U.S. patent application Ser. No. 11/703,997, filed Feb. 8, 2007.

This application is a continuation in part application of U.S. patent application Ser. No. 13/626,518, filed Sep. 25, 2012.

TECHNICAL FIELD

Embodiments described herein are generally in the field of intravascular devices. More particularly, embodiments described herein relate to intravascular catheters having a flexible and manipulatable hinge or joint region.

BACKGROUND

Lasers of various wavelengths coupled to laser fibers for the delivery of laser energy are used in a number of medical procedures. Conventional laser fibers however are not capable of being actuated or deflected to give the operator control of the distal tip of the laser fiber for price placement of the distal laser fiber tip.

INCORPORATION BY REFERENCE

All publications and patent applications mentioned in this specification are herein incorporated by reference to the same extent as if each individual publication or patent application was specifically and individually incorporated by reference.

BRIEF DESCRIPTION OF THE DRAWINGS

FIG. 5 is a table presenting select parameters of modern flexible ureteroscopes.

FIGS. 8A-8I1 show cross-sectional views of catheter shafts displaying the various relative positions of the push-pull wire lumen, main lumen, and optional inflation lumen, under an embodiment.

FIG. 9A shows a cross-sectional side view of another variation of a catheter assembly, under an embodiment.

FIG. 9B shows a detail side view in which a portion of the tubing defining the main lumen extends as an extension past a distal face of the joint region, under an embodiment.

FIG. 9C shows an end view of the flexible joint region, under an embodiment.

FIG. 9D shows a cross-sectional end view of the catheter body illustrating the wire lumen and the main lumen, under an embodiment.

FIGS. 12A to 12C show side, end, and partially removed side views, respectively, of one variation of a control handle for manipulating the push-pull wire, under an embodiment.

FIGS. 12D and 12E show detail views of the wheel and rack, respectively, used to manipulate the push-pull wire, under an embodiment.

DETAILED DESCRIPTION

Figure 1:
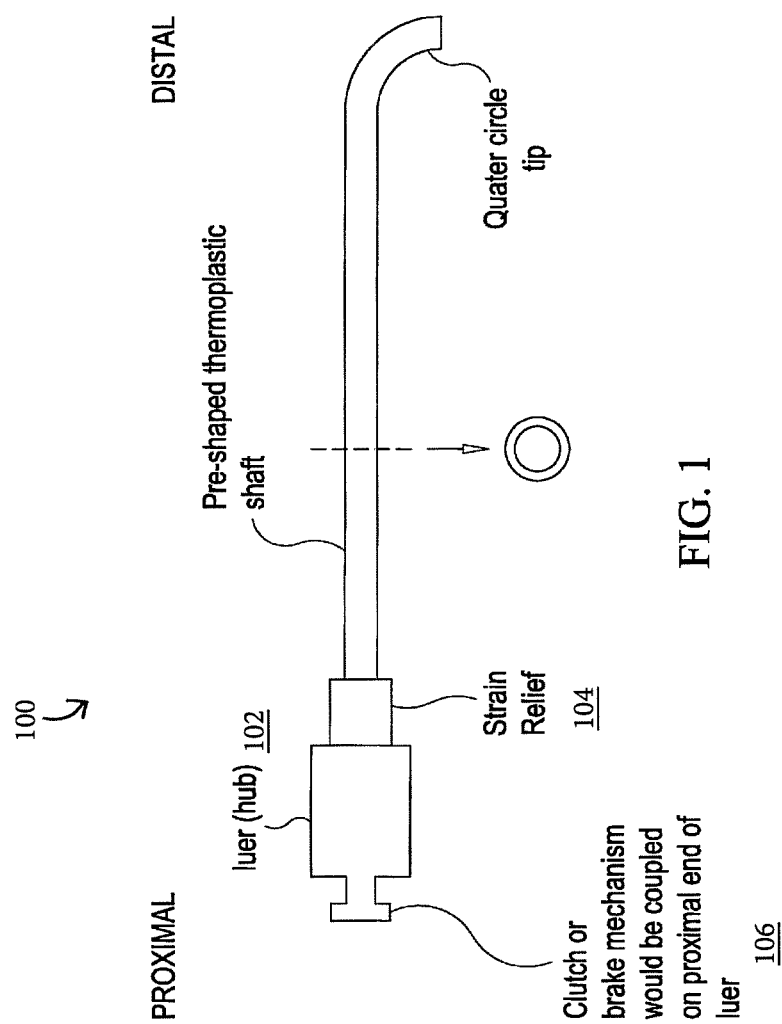
FIG. 1 is a laser fiber catheter or housing, under an embodiment.

Embodiments are described herein comprising lasers of various wavelengths coupled to laser fibers for the delivery of laser energy for use in a number of medical procedures. Embodiments described herein comprise a device including a catheter section having a flexible joint region disposed between a distal end and a proximal end. The device includes a laser fiber disposed within the catheter section. The laser fiber emits laser light at a fiber distal end. The device includes a wire comprising a distal end coupled to the catheter section. The wire is configured to move the distal end of the catheter section from a first position to a second position about the flexible joint region.

In urology, for example, the introduction of lasers and flexible endoscopes has broadened the urological armamentarium for the treatment of various urological conditions. Laser lithotripsy, first used clinically in the late 1980s, uses laser light energy delivered through a quartz laser fiber, directed endoscopically through a working channel of the flexible or rigid endoscope and onto a calculus (stone). A mechanism of action surrounding laser lithotripsy of urological stones occurs via plasma formation between the distal laser fiber tip and the stone, which develops an acoustic shockwave, disrupting the stone along fracture lines. Small quartz fibers, for example 200 and 325 micron core diameter quartz laser fibers, coupled to lasers such as a holmium laser, are passed easily through working channels of ureteroscopes (flexible or rigid endoscopes designed to enter the ureter through the urethra and bladder), fragmenting most stone compositions. The flexible ureteroscope, having distal actuation by operator proximal control, may help the physician generally align the small quartz laser fiber. Many times intraoperatively, additional control for improved placement of the distal laser fiber tip is desired. However, the conventional art as well as commercially available quartz laser fibers do not have a mechanism or mechanisms that allows for proximal control of the distal tip of the laser fiber for precise control and placement against the stone or tissue.

Urologists often use endoscopes in diagnosing and treatment pathology along the urinary tract (kidney, ureter, bladder, urethra). For example, in the case of the ureter (muscular cylindrical conduit, 25 to 30 cm in length, connecting the kidney to the bladder that allows urine to flow from the kidney to the bladder via the ureter), rigid ureteroscopes consist of a long thin tube with channels for irrigation (both inflow and outflow), means to pass a device (working channel), optical system to view the ureter, and light fiber bundle to illuminate the viewing field. The working channel generally has an internal diameter (ID) on the order of 5 French (Fr; 3 Fr=1 mm). The outside diameter (OD) of a rigid ureteroscope generally ranges from 6 Fr to 9 Fr, and is tapered from the proximal to the distal such that the distal tip has the smallest OD when compared to the proximal. Alternatively, flexible ureteroscopes are flexible along the entire working length and, in particular, have an internal actuation mechanism for in-plane deflection of the distal tip on the order of 270°. Generally, flexible ureterscopes have an OD ranging from 8 to 10 Fr and a working channel ID of approximately 3.6 Fr, allowing the use of instruments up to 3 Fr while still permitting adequate irrigation.

The basic components of flexible ureteroscopes include the optical system, deflection mechanism for the distal tip, and working channel. The optical system consists of flexible fiberoptic image and illumination light bundles. Small lenses attached to the proximal and distal ends of the image bundle create a telescope with image magnification, increased field of view, and focusing ability. Improvements in image bundle construction have allowed closer packing of more fibers, resulting in improved images, smaller outer diameters, and larger working channels in both rigid and flexible ureteroscopes. Another design modification of the light bundle is the splitting of this bundle distally into more than one point of light transmission. This permits a more centrally placed working channel as well as better distribution of the light within the working field. FIG. 5 is a table presenting select parameters of conventional flexible ureteroscopes.

The deflection mechanism of flexible ureteroscopes permits maneuverability within the urinary tract system. Most deflecting mechanisms consist of control wires running along the length of the ureteroscope and are attached on the proximal end to a manually operated lever mechanism. The wires traverse along the length of the ureterscope an distally the wires run through moveable metal rings to the distal tip where they are fixed. Moving a proximal lever up or down will pull the control wire and move the tip. When the tip moves in the same direction as the lever, the deflection is "intuitive" (i.e., moving the proximal lever down deflects the distal tip down and moving the proximal level up moves the distal up). Modern flexible ureteroscopes allow both up and down deflection in a single plane. This plane of deflection is marked by the reticle seen as a notch within the field of view of the ureteroscope. Modern flexible ureteroscopes permit down deflection of approximately 180°.

A study investigating the angle between the major axis of the ureter and the lower pole infundibula (ureteroinfundibular angle) reported the average angle to be 140° with a maximum of 175°. Active deflection of the ureteroscope of 180° is necessary to allow visualization of the lower pole in most patients. However, reaching into the lower pole calyx with the tip of the ureteroscope can be difficult.

The flexible ureteroscopes have a more flexible segment or joint of the ureteroscope due to a material and/or structural changes of the sheath such as durometer, located just proximal to the point of active deflection (joint). The ability to engage the passive secondary deflection depends upon the ability to passively bend this portion of the ureteroscope off of the superior portion of the renal pelvis for example. This can be difficult or impossible in patients with significant hydronephrosis. Additionally, once the tip of the ureteroscope has been extended into the lower pole calyx, the ability to manipulate working instruments and work within the calyx, using active primary deflection, can be challenging.

Conventional deflecting mechanism technology attempted to overcome this deficiency. The DUR-8 Elite (Gyms ACMI, Stamford, Conn., USA) is a flexible ureteroscope that incorporates active secondary deflection. In addition to the active primary deflection (185° down, 175° up) the secondary deflection is now active, 165° down. It is controlled with an additional lever opposite the existing primary deflection lever and can be locked in place. Secondary deflection is not dependent upon passive manipulation of the scope off of the upper portion of the renal pelvis. The degree of secondary deflection is not dependent upon the position of the scope or resistance to advance the scope but is controlled with the deflecting lever. Severe hydronephrosis will not prevent the use of secondary deflection.

Locking the secondary deflection in place can simplify manipulation of the primary deflection within the lower pole calyx. The usefulness of this active secondary deflection of the DUR-8 Elite was evaluated and it was found that the dual deflecting DUR-8 Elite ureteroscope was helpful in cases in which the single deflection flexible instruments fail to access and treat upper urinary tract pathology.

Karl Storz Endoscopy (Tuttlingen, Germany) has introduced "exaggerated deflection" with their Flex-X model flexible ureteroscope. This modification of the deflection mechanism permits active primary deflection to 300°. When approaching the lower pole calyx, the tip will extend out as it is deflected against the lower pole infundibulum.

Ureteral stones that cannot be extracted in total are candidates for fragmentation via ureteroscopic lithotripsy including electromechanical lithotripsy (e.g. Lithoclast, Boston Scientific), electrohydraulic lithotripsy (EHL), and laser lithotripsy (holmium laser lithotripsy). Laser lithotripsy has the advantage of minimizing trauma to the ureter and reducing stone dislocation. The holmium laser has dramatically improved intraluminal lithotripsy and has become the intraluminal lithotripsy energy of choice for most urologists. The holmium laser has a wavelength of 2,100 nm, which is absorbed in 3 mm of water and 0.4 mm of tissue, making it very safe for use in urology. Fragmentation of the stone occurs via a photothermal reaction within the crystalline matrix of stone. By not relying upon shockwave generation for stone fragmentation, the photothermal reaction produces stone dust rather than fragments, effectively removing a moderate volume of the stone. Small quartz laser fibers can be used with both rigid and flexible ureteroscopes to deliver laser energy from the holmium laser to the stone. Quartz laser fibers are available in various sizes. The most common fibers used range from core sizes of 200 microns to 325 microns. None of the currently available laser fibers, however, have a mechanism or mechanisms that allows for proximal control of the distal tip of the fiber to steer, manipulate, and/or control the deflection or actuation of the distal tip for precise placement against the stone.

Benign prostatic hyperplasia (BPH) is the most prevalent disease entity in elderly men. In the late 1980s, lasers became a novel way to open a wider channel and improve voiding dynamics. Many different techniques under the term laser prostatectomy have evolved. Individual techniques may vary greatly, but the two main tissue effects include coagulation and vaporization. Coagulation occurs when somewhat diffusely focused laser energy heats tissue and temperatures reach as high as 100° C. Proteins denature and necrosis ensues, resulting in subsequent sloughing of necrotic tissue (i.e., a debulking of the prostate). This process may take as long as several weeks to complete and often initially results in edema, which transiently increases prostate volume (and therefore may require short-term urethral catheterization).

The principle representative procedures in the laser coagulation category include visual laser ablation of the prostate (VLAP) using Nd:YAG and interstitial laser coagulation (ILC). VLAP uses a direct transurethral viewing source (cystoscope and coupled to a video camera) along with a laser that is supplemented by a visible (usually helium-neon) aiming beam. Interstitial coagulation using a diode laser is another coagulative technique in which optical fibers are introduced transurethrally or perineally directly into the prostate. This can cause large-volume necrosis with atrophy while preserving the urethral mucosa.

In several studies these coagulative procedures have proven to have unacceptably high adverse events, namely irritative voiding, dysuria, and other storage symptoms, as well as high reoperation rates. Additionally, more efficient and improved laser applications such as Ho:LEP and photo-vaporization (PVP) techniques have shown to be more effective largely replacing VLAP and ILC. Vaporization occurs when greater laser energy is focused (increased power density) and tissue temperatures reach as high as 300° C. This causes tissue water to vaporize and results in an instantaneous debulking of prostatic tissue. The high-power (80-W) potassium-titanyl phosphate laser (KTP or Greenlight) is commonly used for its vaporization effects on prostate tissue. This procedure is associated with significantly less bleeding and fluid absorption than standard transurethral prostate resection. Because of this, the KTP laser is safely used in seriously ill patients or those receiving oral anticoagulants. Additionally, the KTP laser's ease of use has made it an attractive option for urologists. Drawbacks to the KTP procedure compared with traditional TURP include the lack of tissue obtained for postoperative pathological analysis and the inability to diagnose and unroof concomitant prostatic abscesses.

A higher-powered 120-W LBO laser (GreenLight HPS) was developed and even more recently the 180-W LBO system (GreenLight XPS) has been marketed to improve upon current vaporization speed. Whether these newer generation KTP lasers are clinically superior to their predecessor remains to be seen.

Laser energy has been used to incise or enucleate prostate adenomas down to the capsule, making this procedure the endoscopic analog of open simple prostatectomy. The Ho:YAG is ideally suited for this task because it creates precise incisions, cuts by vaporizing tissue with adequate hemostasis, and leaves minimal collateral damage. Advantages of this method include the availability of a specimen for histologic examination, less postoperative catheter time, and the ability to excise large adenomas. Drawbacks include greater training time and the need to transport the adenoma (in toto or portioned) into the bladder to morcellate it prior to removal.

For some time, the criterion standard treatment for BPH has been TURP and the standard by which all of the above techniques are compared. TURP is used less frequently because of associated complications, including bleeding and transurethral resection (TUR) syndrome and the improved efficacy of medical therapies. Additionally, the preponderance of urology patients taking chronic oral anticoagulants and anti-platelet therapy mandate the need for techniques that can be safely performed in this setting. In general, the laser prostatectomies mentioned above have added safety and less perioperative pain compared with TURP. Less bleeding occurs and the operative time is usually less; therefore, most types may be performed on patients who are receiving anticoagulants.

Laser modalities are safer than TURP in the perioperative period, although some may have a similar long-term complication profile. The coagulative approaches have been largely abandoned because of post-operative symptomatology and the availability of other modalities. Vaporization techniques, particularly Greenlight PVP, have achieved widespread popularity, largely because of their ease of use and the ability to perform these procedures on an outpatient basis. HoLAP is also a viable vaporization technique and in fact a RCT showed essentially equivalent efficacy and complication rates when compared with Greenlight PVP. Only operative time favored PVP. HoLAP requires the most technical expertise with a correspondingly steep learning curve but is likely the optimal endoscopic approach to the very large gland. Although all of the modalities mentioned are efficacious, none is efficacious enough to make the old-fashioned TURP obsolete.

In all of the aforementioned laser procedures for the treatment of BPH, none of the laser fibers used in these procedures can be actuated or deflected to give the operator control of the distal tip of the laser fiber for price placement of the distal laser fiber tip.

Various laser energies have been used to treat bladder and upper urinary tract urothelial tumors. Most commonly, holmium and Nd:YAG are used in this setting. Quartz laser fibers are directed endoscopically to deliver laser energy to the tissue. The Nd:YAG laser energy is used to coagulate and ablate with a thermal effect that extends deeper than other lasers. Holmium is more precise, with less of a coagulative effect. The advantages of laser therapy for tumor ablation include less bleeding and, as such, catheter drainage is usually unnecessary. A lower incidence of stricture formation results when compared with electrocautery because fibrotic reaction is minimal. The laser technique decreases the need for anesthesia, causes less postoperative pain, and allows a quicker return to work. The Ho:YAG laser can be used through a flexible cystoscope to ablate recurrent superficial bladder tumors in an office setting. A recent review of patients treated with the flexible cystoscope reported a high degree of satisfaction because this method avoided the need for general anesthesia and reduced post-operative pain. No pathology specimen is available, thus, determining depth of invasion is impossible unless multiple prior biopsy samples were obtained. Another drawback, especially with the Nd:YAG laser, is that the area of destruction is deep and not fully visualized. Some reports of bowel perforation exist when treating bladder dome lesions even without visible bladder perforation secondary to the effect of Nd:YAG. In this setting, Ho:YAG is a better choice. In all of the aforementioned laser procedures for the treatment of urothelial malignancies, however, none of the laser fibers used in these procedures can be actuated or deflected to give the operator control of the distal tip of the laser fiber for price placement of the distal laser fiber tip.

Urethral strictures have been a frustrating entity for the urologist to treat. Many different procedures are available to deal with them, but all of them, except open urethral reconstruction, are associated with a high rate of recurrence. Internal urethrotomy yields a success rate of only 20-40%, and repeat procedures, unfortunately, offer little improvement. Nd:YAG, KTP, and Ho:YAG lasers have all been used experimentally to vaporize fibrous strictures. They can yield recurrence rates similar to those of the cold-knife internal urethrotomy. Recently, some hope of using an Nd:YAG laser with a crystal contact tip at the end of a delivery fiber has occurred. In a study of 42 patients with urethral strictures, the Nd:YAG crystal tip contact method of vaporization yielded a 93% success rate that was durable for a mean of over 2 years. However, in all of the aforementioned laser procedures for the treatment of urothelial stricture disease, none of the laser fibers used in these procedures can be actuated or deflected to give the operator control of the distal tip of the laser fiber for price placement of the distal laser fiber tip.

Similarly, in other rigid scope procedures such as arthroscopy of the knee or endoscopic procedures of the abdomen, the availability of a deflectable or actuated laser fiber would improve these and other endoscopic surgical procedures by offering the physician laser distal tip control to accurately and/or efficiently place the fiber in a desired position or location for laser treatment.

While preferred embodiments of the present invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Figure 2:
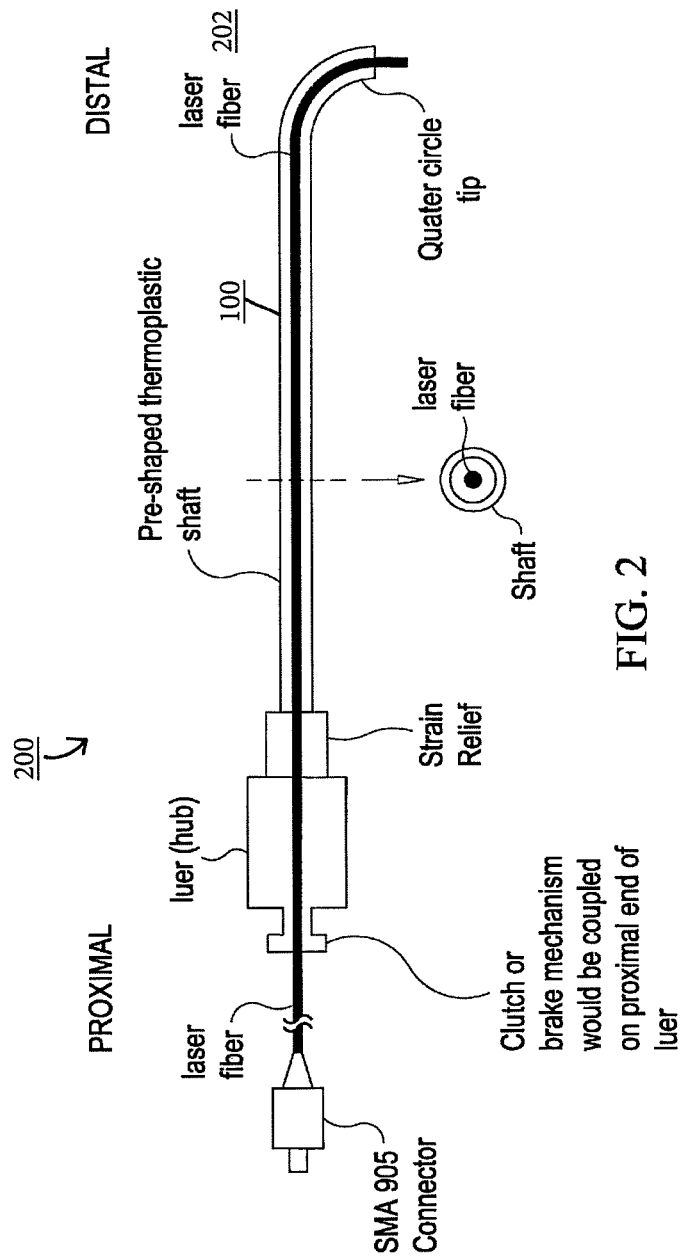
FIG. 2 is a laser fiber system comprising the pre-shaped laser fiber catheter including a lumen, and a laser fiber traversing at least a portion of the lumen, under an embodiment.

FIG. 1 is a laser fiber catheter or housing 100, under an embodiment. The laser fiber catheter 100 comprises a pre-shaped laser fiber catheter, but is not so limited. FIG. 2 is a laser fiber system or assembly 200 comprising the pre-shaped laser fiber catheter 100 including a lumen, and a laser fiber 202 traversing at least a portion of the lumen, under an embodiment. In this embodiment, the laser fiber system 200 comprises a first component that is the deflectable and controllable catheter or housing 100, and a second component that is a laser fiber 202. The laser fiber 202 is reversibly placed into at least a portion or segment of the lumen of the deflectable and controllable laser fiber catheter 100, but is not so limited.

The pre-shaped laser fiber catheter 100 of the laser fiber system 200 comprises a single lumen catheter or tube fabricated from materials that include one or more of thermoplastic polymers or polymer blends (e.g., polyurethane and polyamide, etc.), with a luer or hub 102 and strain relief component 104 positioned at a proximal end or region of the catheter. The pre-shaped laser fiber catheters are available in various lengths where, in an embodiment, the lengths are in a range of approximately 0.25 meters (m) to 3.0 meters. The laser fiber catheters accept laser fibers 202 of various diameters, for example, a diameter of approximately 160 microns. The thermoplastic polymer catheters 100 of an embodiment are pre-shaped to form one or more distal tip shapes, for example semi-circular distal tip configuration, and semi-oval distal tip configuration to name a few. The physician or operator of the laser fiber system can also shape the distal tip of the catheter to a shape appropriate to one or more of a procedure in which the system is to be used and a region of a biological entity in which the system is to be used.

The laser fiber 202 is inserted through the hub 102 on the proximal end of the catheter and pushed through a length of the pre-shaped catheter 100 until the distal end of the laser fiber emerges from the distal end of the catheter. The hub 102 of an embodiment includes a clutch or brake mechanism 106 such that once the laser fiber 202 is positioned within and through the catheter 100 at the desired position, the clutch or brake mechanism 106 is actuated, engaging and fixing the desired position of the laser fiber 202. The combination of the pre-shaped catheter 100 and the laser fiber 202 is referred to as the laser fiber system 200 but is not so limited.

An example of an operational scenario involving use of the laser fiber system includes laser lithotropsy of a ureteral stone. In this procedure, the laser fiber system is placed into the working channel of the flexible or rigid ureteroscope via the working channel port. As the laser is pushed distally into working channel, it emerges from the distal end of the ureteroscope such that it is positioned adjacent to the ureteral stone. For a given fixed position of the ureteroscope, the laser fiber system can be accurately placed in the surgical field of view by pushing or pulling the laser fiber system and, if needed, torquing the laser fiber system, as described in detail herein.

An alternative embodiment of the laser fiber device herein includes a laser fiber endoscope or housing. The endoscope of this embodiment is a medical device comprising a long, thin, flexible (or rigid) tube that includes a light and a video camera. More particularly, the endoscope of an embodiment comprises a rigid or flexible tube, a light delivery system to illuminate the organ or object under inspection, a lens system transmitting the image from the objective lens to the viewer (e.g., a relay lens system in rigid endoscopes, or a bundle of optical fibers in a fiberscope), an eyepiece, and an additional lumen or channel to allow entry of medical instruments or manipulators. The lumen of the endoscope houses at least one laser fiber. The laser fiber is inserted through an opening or channel at the proximal end of the endoscope and pushed through a length of the endoscope until the distal end of the laser fiber emerges from the distal end of the endoscope. In this embodiment, the combination of the endoscope and the laser fiber is referred to as the laser fiber system but is not so limited. The laser fiber endoscope described herein can be used in any field of endoscopy, including but not limited to endoscopy of the gastrointestinal tract (GI tract) (e.g., oesophagus, stomach and duodenum (esophagogastroduodenoscopy), small intestine (enteroscopy), large intestine/colon (colonoscopy, sigmoidoscopy), magnification endoscopy, bile duct (endoscopic retrograde cholangiopancreatography (ERCP), duodenoscope-assisted cholangiopancreatoscopy, intraoperative cholangioscopy), rectum (rectoscopy) and anus (anoscopy) (collectively referred to as proctoscopy)), respiratory tract (e.g., nose (rhinoscopy), lower respiratory tract (bronchoscopy)), ear (e.g., otoscope), urinary tract (e.g., cystoscopy), female reproductive system (gynoscopy) (e.g., cervix (colposcopy), uterus (hysteroscopy), fallopian tubes (falloposcopy)), normally closed body cavities (e.g., using a small incision) (e.g., abdominal or pelvic cavity (laparoscopy), interior of a joint (arthroscopy), organs of the chest (thoracoscopy and mediastinoscopy)), during pregnancy (e.g., amnion (amnioscopy), fetus (fetoscopy)), plastic surgery, panendoscopy (triple endoscopy, combines laryngoscopy, esophagoscopy, and bronchoscopy), orthopedic surgery (e.g., hand surgery, such as endoscopic carpal tunnel release, epidural space (epiduroscopy), bursae (bursectomy)), endodontic surgery (e.g., maxillary sinus surgery, apicoectomy), and non-medical uses for endoscopy (e.g., pre-visualization of scale models (architectural endoscopy), internal inspection of complex technical systems (borescope), examination of improvised explosive devices by bomb disposal personnel, surveillance via tight spaces).

The laser fiber catheter comprises a pre-shaped laser fiber catheter, but is not so limited. FIG. 2 is a laser fiber system or assembly comprising the pre-shaped laser fiber catheter including a lumen, and a laser fiber traversing at least a portion of the lumen, under an embodiment. In this embodiment, the laser fiber system comprises a first component that is the deflectable and controllable catheter or housing, and a second component that is a laser fiber. The laser fiber is reversibly placed into at least a portion or segment of the lumen of the deflectable and controllable laser fiber catheter, but is not so limited.

The pre-shaped laser fiber catheter of the laser fiber system comprises a single lumen catheter or tube fabricated from materials that include one or more of thermoplastic polymers or polymer blends (e.g., polyurethane and polyamide, etc.), with a luer or hub and strain relief component positioned at a proximal end or region of the catheter. The pre-shaped laser fiber catheters are available in various lengths where, in an embodiment, the lengths are in a range of approximately 0.25 meters (m) to 3.0 meters. The laser fiber catheters accept laser fibers of various diameters, for example, a diameter of approximately 160 microns. The thermoplastic polymer catheters of an embodiment are pre-shaped to form one or more distal tip shapes, for example semi-circular distal tip configuration, and semi-oval distal tip configuration to name a few. The physician or operator of the laser fiber system can also shape the distal tip of the catheter to a shape appropriate to one or more of a procedure in which the system is to be used and a region of a biological entity in which the system is to be used.

The laser fiber is inserted through the hub on the proximal end of the catheter and pushed through a length of the pre-shaped catheter until the distal end of the laser fiber emerges from the distal end of the catheter. The hub of an embodiment includes a clutch or brake mechanism such that once the laser fiber is positioned within and through the catheter at the desired position, the clutch or brake mechanism is actuated, engaging and fixing the desired position of the laser fiber. The combination of the pre-shaped catheter and the laser fiber is referred to as the laser fiber system but is not so limited.

An example of an operational scenario involving use of the laser fiber system includes laser lithotropsy of a ureteral stone. In this procedure, the laser fiber system is placed into the working channel of the flexible or rigid ureteroscope via the working channel port. As the laser is pushed distally into working channel, it emerges from the distal end of the ureteroscope such that it is positioned adjacent to the ureteral stone. For a given fixed position of the ureteroscope, the laser fiber system can be accurately placed in the surgical field of view by pushing or pulling the laser fiber system and, if needed, torquing the laser fiber system, as described in detail herein.

Figure 3:
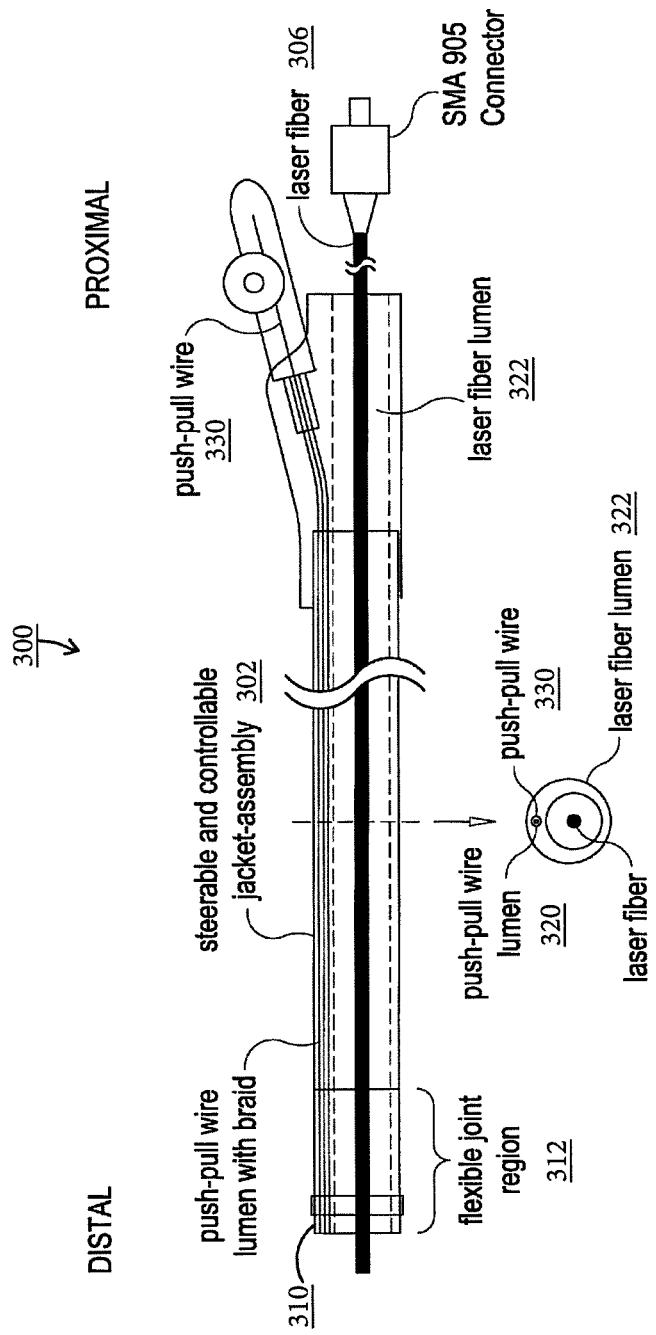
FIG. 3 is a laser fiber system comprising a steerable and controllable laser fiber catheter including a lumen, and a laser fiber traversing at least a portion of the lumen, under an alternative embodiment.
Figure 4:
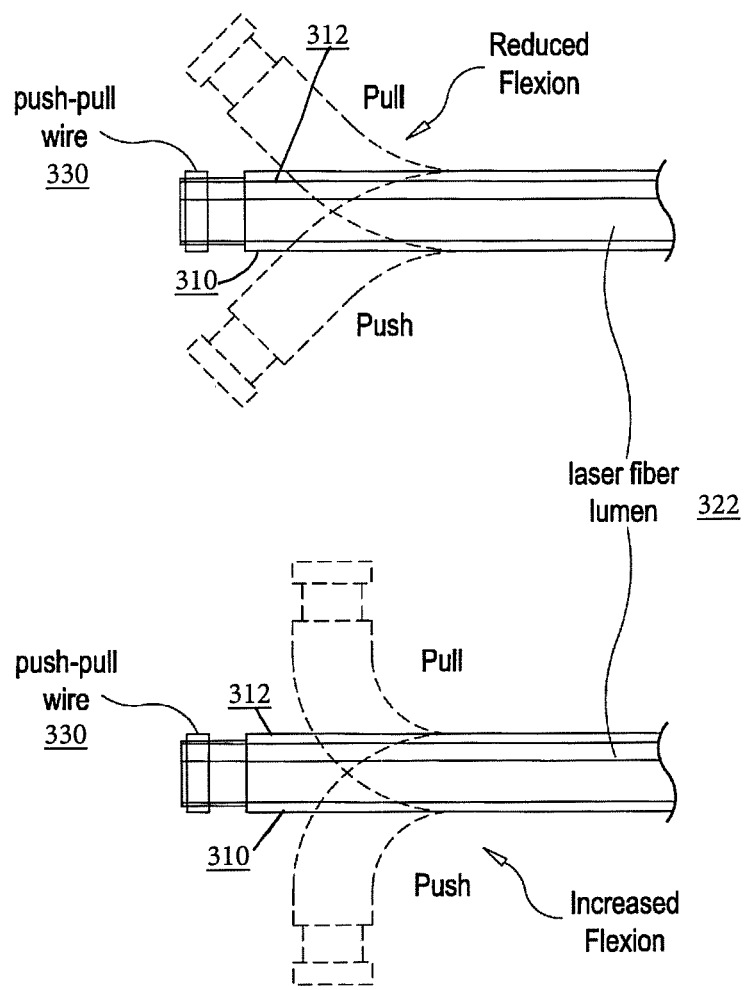
FIG. 4 shows deflection of a distal tip of the steerable and controllable laser fiber system, under an embodiment.

FIG. 3 is a laser fiber system 300 comprising a steerable and controllable laser fiber catheter 302 including a lumen 322, and a laser fiber 306 traversing at least a portion of the lumen 322, under an alternative embodiment. In this embodiment, the laser fiber system 300 comprises a first component that is the steerable and controllable catheter or housing 302, and a second component that is the laser fiber 306. The laser fiber 306 is reversibly placed into at least a portion or segment of the lumen 322 of the steerable and controllable laser fiber catheter 302, but is not so limited. FIG. 4 shows deflection of a distal tip 310 of the steerable and controllable laser fiber system 300, under an embodiment.

The steerable and controllable catheter 302 of the laser fiber system comprises a flexible joint region 312 that defines a main lumen and at least one wire lumen. The flexible joint region 312 is located at a distal end or region of the steerable and controllable catheter assembly and is configured to be more flexible when compared to the assembly proximal to the joint. The flexible joint region 312 has a predetermined length configured or sized to affect or control a flexure (e.g., reduced stiffness) of the flexible joint region 312. The wire lumen 320, in an embodiment, is positioned adjacent to the main lumen 322, but is not so limited. The main lumen 322 houses the laser fiber 306 but is not so limited. The wire lumen 320 defines an opening at or near a distal region or end of the flexible joint region. The laser fiber system includes a push-pull wire 330 positioned in at least a portion of the wire lumen 320 and configured to be pushed or pulled along a longitudinal axis of the wire lumen 320.

The wire lumen of an embodiment comprises a braided or non-braided lumen, as described in detail herein. When the braided lumen is used, the braid may traverse a portion or segment of the lumen or an entire length of the lumen. Furthermore, the braid configuration of an embodiment may be constant and uniform or, alternatively, comprise a varied braid pitch resulting in changes in stiffness. The braid may be made from a number of materials, for example, superelastic alloys, but is not so limited.

The deflection or movement of the flexible joint is controlled in an embodiment by a push-pull wire such that it deflects when the push-pull wire is moved or manipulated at the proximal aspect of the catheter assembly. The flexible joint may be varied to extend beyond the braid termination, or it may be extended to the deflecting portion to encompass a portion of the braid. By varying the length of the flexible joint region, the radius or amount of curvature or joint flexure region can be controlled. For example, a joint region having a relatively shortened length between the distal end of the joint region and the terminal end of the braid allows for reduced flexion relative to a neutral position of the steerable and controllable laser fiber assembly. A lengthened joint region extending to a more proximally located terminal end facilitates more flexion when compared to a shorter joint region. As such, flexure may be controlled in part by the length of the flexible joint region. To further facilitate flexion of the laser fiber assembly and control of bending, additional members such as coils may be incorporated into the transition region of the laser fiber system assembly.

The laser fiber system of an alternative embodiment includes a wire attachment band at or near the distal end or region of the flexible joint region. The wire attachment band secures the push-pull wire to the distal end or region. Again, the flexible joint region has a predetermined length configured or sized to affect or control a flexure (e.g., reduced stiffness) of the flexible joint region.

The laser fiber system of another alternative embodiment comprises two or more longitudinal lumens, but is not so limited. The two lumens include a first lumen running the length of the assembly and housing the laser fiber, and a second lumen running at least a portion of the length of the assembly and housing the push-pull wire. The steerable and controllable laser fiber assembly can have a consistent and constant cross section throughout its length or, alternatively, the cross section may vary from proximal to distal end. Furthermore, the material properties of the polymer of the steerable and controllable laser fiber assembly may vary along the length so as to vary the column stiffness. For example, the proximal third of the laser fiber assembly may be stiffer when compared to the middle third of the laser fiber assembly, but the embodiment is not so limited.

The fiber catheter or housing of the embodiments described above comprises a catheter or catheter section that includes a main lumen, a wire lumen housing a push-pull wire, and a flexible joint region. The catheter section includes a control including a handle and a wire control member engaging the push-pull wire for manipulating the flexible joint region. The push-pull wire may be tapered, having a proximal portion of a first diameter and a smaller diameter distal portion. A coil may be placed around the smaller diameter to prevent buckling of the smaller diameter portion. A strapping coil may also disposed around the outside of the catheter, and an outer covering may be disposed around the strapping coil. An outer covering of a mesh may also be disposed around the distal tip of the catheter. Descriptions of the catheter or catheter section of an embodiment follow.

The catheter of an embodiment involves a multi-lumen catheter. The device may optionally include a balloon member. The catheter includes a shapeable, flexible distal section which may be in the vicinity of the balloon, if the balloon member is utilized. The flexible section, or "hinge region", is manipulated from outside the body during the process of delivering the vaso-occlusive device or material. The terms "hinge region", "hinge", or "flexible joint" may be used interchangeably.

Figure 6A:
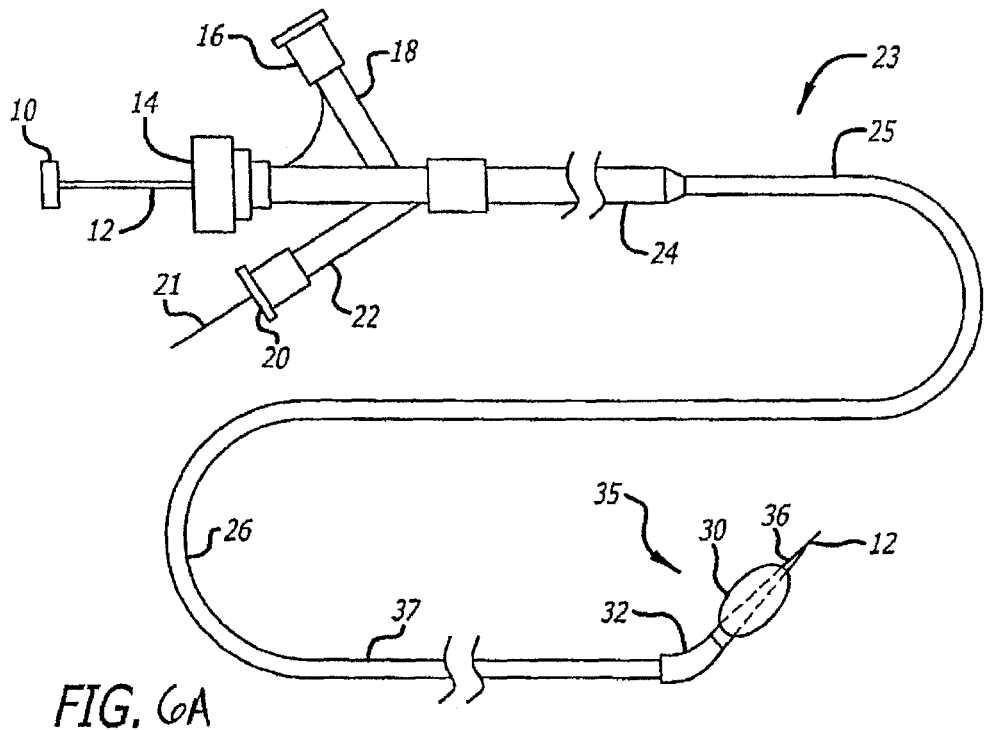
FIG. 6A shows an external view of one variation of the catheter assembly, under an embodiment.

FIG. 6A shows a catheter assembly 23, under an embodiment. This variation of the catheter assembly 23 includes a catheter shaft 25 comprising a flexible, thin walled body or tube 26 having an inner lumen which extends between proximal and distal catheter ends 24, 37, respectively. The tube 26 generally comprises a nondistensible polymer having the appropriate mechanical properties for this application, for example polyethylene (e.g., HDPE, LDPE, LLDPE, MDPE, etc.), polyesters (such as Nylon), polypropylene, polyimide, polyvinyl chloride, ethylvinylacetate, polyethylene terephthalate (PET), polyurethane (e.g., TEXIN such as that made by Bayer Corporation), PEBAX, fluoropolymers, such as polytetrafluoroethylene (PTFE), for example, mixtures of the aforementioned polymers, and their block or random co-polymers.

The catheter assembly can be used for access through the vasculature to the brain often, but not necessarily, using a guide wire. If an optional balloon member is included in the catheter assembly, the balloon member may be inflated to close or to restrict any hollow body lumen, such as an artery, vein, orifice, cavity, etc., or the mouth of an aneurysm prior to or during placement of a vaso-occlusive device. Generally, the assembly may be flexed at a "hinge region" near or at the distal end of the catheter by a push-pull wire extending proximally through the catheter. A main lumen defined through the catheter assembly can be used for the introduction of a vaso-occlusive device or material for eventual placement in the vasculature.

The proximal catheter end 24 of an embodiment includes a fitting 18 (e.g., a "LuerLok") through which fluid may be supplied to the catheter's inflation lumen through a side port 16. The proximal end of the catheter is provided with a second port 20 and a fitting 22 through which the push-pull wire is used to manipulate the hinge region 32 in the distal catheter tip. The proximal end fitting 18 includes an axially extending port 14 which communicates with the delivery/guide wire lumen of the catheter. The optional guide wire 12 may have any suitable construction for guiding the flexible catheter to its intended site within the body. The proximal end of the guidewire 12 of an embodiment includes a handle 10 for applying torque to the guidewire 12 during catheter operation, as described in further detail herein. The guidewire may have a variable stiffness or stepped diameter along its length, for example, a larger-diameter, stiffer proximal region and one or more smaller-diameter, more flexible distal regions.

The distal portion 35 of the catheter may include an optional inflatable member 30, for example a balloon. An opening 36 at the distal end of the catheter may also be used for delivery of drugs and/or vaso-occlusive devices to a pre-selected vascular site. The distal end region 35 of the catheter 25 of an embodiment includes an inflatable balloon 30 which, when inflated, aids in the placement of vaso-occlusive materials or devices by blocking the entrance to the aneurysm or the artery adjacent to the aneurysm.

Figure 6B:
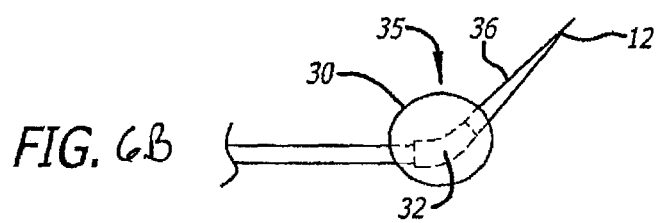
FIGS. 6B and 6C show alternative configurations of the distal region of the catheter assembly, under an embodiment.
Figure 6C:
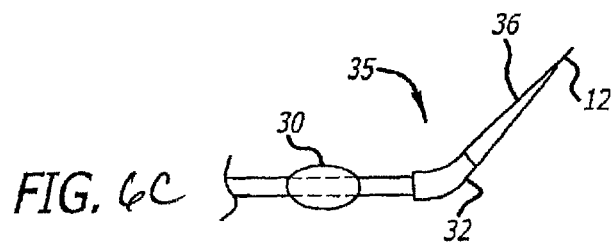

Use of the balloon member is optional. When a balloon is used the balloon wall section (described in detail herein) is formed from a thin sleeve of polymeric material and attached at its opposite sleeve ends to a relatively more rigid tube section. FIGS. 6A, 6B, and 6C display various configurations of the distal catheter tip 35 positioning based on the placement of the flexible hinge region. FIGS. 6A, 6B, and 6C, respectively, show variations of the catheter 23 in which the hinge region 32 is placed proximal to (FIG. 6A), within (FIG. 6B), and distal to (FIG. 6C) the inflatable member region 30 when such an inflatable member 30 is included in the catheter assembly. Flexion of the hinge region is achieved through remote manipulation of the push-pull wire 21, but is not so limited.

FIGS. 7A through 7D show variations of the distal end region 35 and hinge region 32 of the catheter described above with reference to FIGS. 6A, 6B, and 6C. The catheter tube 40 of FIG. 7A may have an inflatable member 44, e.g., a balloon, formed by an inflatable sleeve secured at its ends 41, 43 to the catheter tube wall 40. The inflatable member or balloon 44 may be of a shape, thickness, and material as is typical of balloons used in neurovascular balloon catheters. The inflatable member or balloon 44 may be formed of a thin polymeric material, and/or an elastomeric, stretchable material such as silicone rubber, latex rubber, polyvinyl chloride, complex co-polymers such as styrene-ethylene butylene-styrene copolymers such as C-FLEX, or alternatively, a non-stretchable film material such as polyethylene, polypropylene, or polyamides such as Nylon. Attachment of the sleeve ends to the catheter tube may be by adhesives, heat shrinkage, mechanical fasteners, or other suitable method. Inflation lumen 42, which is also optional if balloon 44 is included in the assembly, allows communication between the inflation fluid source and the balloon 44 through at least one opening 50 formed in the catheter tube 40. Inflation and deflation of the balloon are effected by the passage of radio-opaque fluid, saline, or other fluid. A push-pull wire lumen 60 may extend throughout the catheter tube 40 to protect the passage of the push-pull wire 62. To assist in preventing collapse of the tube 60 enclosing the push-pull wire 62 and to prevent kinking or bulging during actuation, the push-pull wire lumen 60 may have additional structure provided by a layer of higher stiffness polymer (e.g., a polyimide), a support coil, or a support braid, as described in detail herein.

Manipulation of the push-pull wire 62 via the proximal wire port 20 in FIG. 6A may result in flexion of the distal end 35 of the catheter 25. The guidewire 57 may extend through the delivery lumen 55 which lies interior to the catheter tube 40. The push-pull wire 62 may extend through the push-pull wire lumen 60 and may be attached to radio-opaque band 67, which may surround the catheter distal end 65 and may be made of a variety of radio-opaque material such as stainless steel, platinum, gold, nickel, etc. The hinge region 58 at which the distal catheter tip 65 flexes due to proximal manipulation of the push-pull wire 62 may be located proximal to, within, or distal to the balloon (if used), as displayed respectively in FIGS. 7A, 7B, and 7C. Although the inclusion of a balloon with the catheter assembly is described herein, the balloon is optional and may be omitted entirely from the catheter assembly.

Figure 7A:
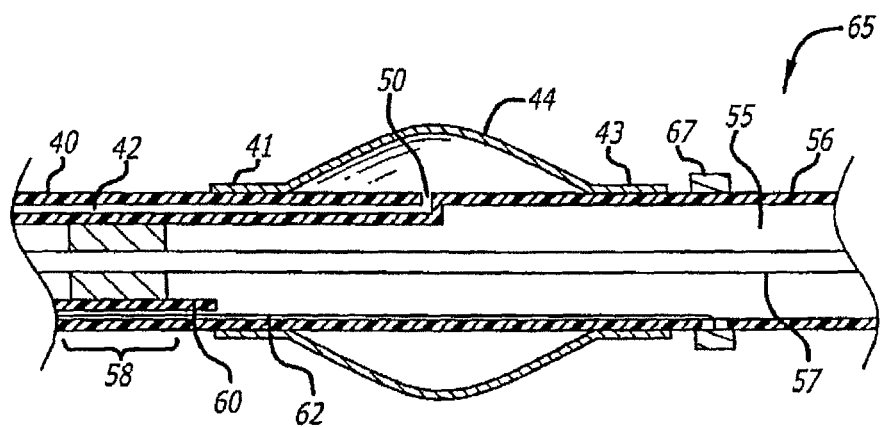
FIG. 7A shows a cross sectional view of a proximally placed hinge region in a variation of the distal region of the catheter assembly, under an embodiment.
Figure 7B:
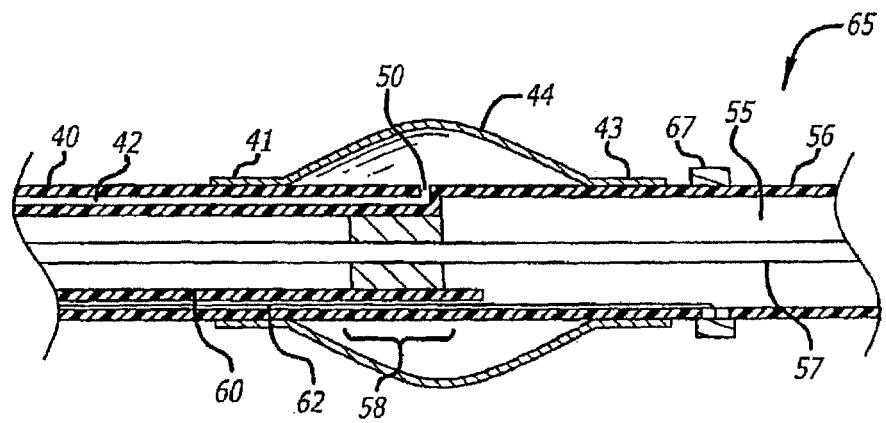
FIG. 7B shows a cross sectional view of a mid-balloon hinge region placement for another variation of the distal region of the catheter assembly, under an embodiment.
Figure 7C:
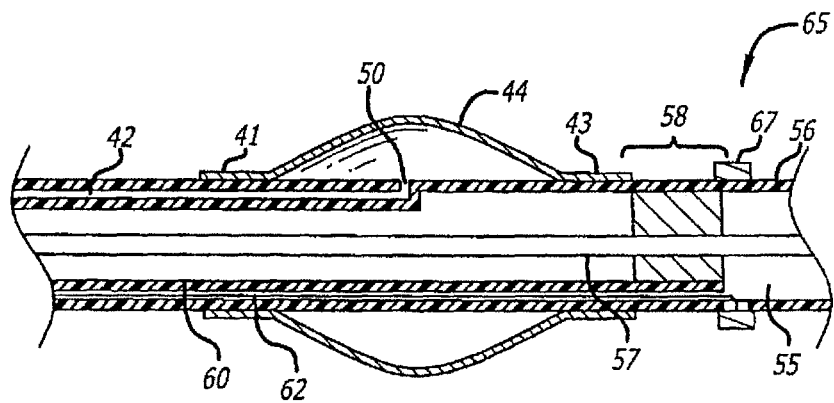
FIG. 7C shows a cross sectional view of a distally placed hinge region in another variation of the distal region of the catheter assembly, under an embodiment.

As shown in FIG. 7A, when the hinge region 58 is placed proximally of the balloon 44, the push-pull wire lumen 60 extends to a region which is proximal of the distal end of the balloon 44 to allow flexion of the region of the catheter's distal end 65 which includes the entire balloon 44. If the hinge region 58 is placed interior to the balloon, as in FIG. 7B, flexion of the catheter's distal end 65 occurs such that the point of flexion is within the balloon (also displayed in FIG. 6B). FIG. 7C shows the placement of hinge 58 distal to the balloon; flexion during distal-hinge placement occurs such that the manipulatable region of the catheter's distal end 65 does not include any portion of the balloon 44.

Figure 7D:
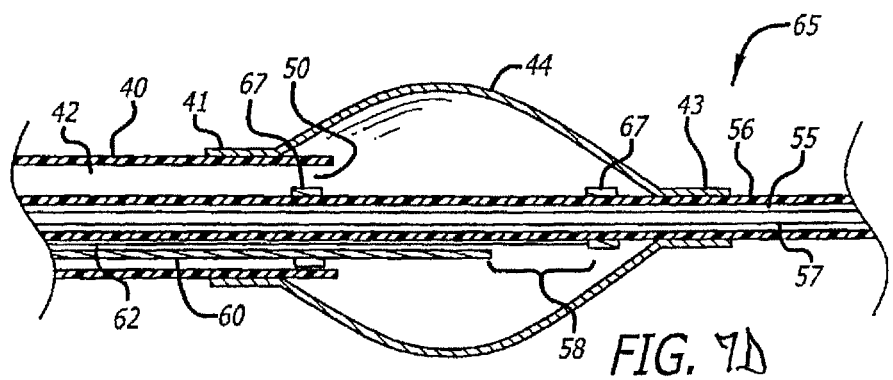
FIG. 7D shows a cross sectional view of an additional mid-balloon hinge region placement for another variation of the distal region of the catheter assembly, under an embodiment.

FIG. 7D shows placement of the hinge region 58 interior to the balloon 44. The balloon 44 extends between the guidewire/delivery tube 56 and the outer catheter tube 40 enclosing the annular inflation lumen 42. The push-pull wire 62 is attached to the distal end 65 of the guidewire/delivery lumen tube 56. In each of the variations shown in FIGS. 7A to 7D, the push-pull wire 62 may be attached at its distal end to the catheter through a variety of methods, for example, adhesives, crimping, and mechanical fasteners, to name a few. In this variation, a radio-opaque marker band 67 may be used to anchor the wire 62. Moreover, other attachment sites may be used for attachment of the push-pull wire 62 distal to the hinge region 58. The push-pull wire itself is a wire which has sufficiently high column and tensile strengths such that it may be pushed or pulled along a longitudinal axis of the wire through the wire lumen without buckling or kinking. It may be fabricated into a wire having a circular cross-section, although other cross-sectional shapes may be utilized, having a diameter, for instance, ranging from 0.025 mm and higher. The push-pull wire may be fabricated from a biocompatible metallic material such as stainless steel, platinum, etc. Alternatively, the push-pull wire 62 may also include a tapered wire which has a larger diameter at or near its proximal end and a smaller diameter at or near its distal end. Conventional guidewires may also be utilized as a push-pull wire, provided that it has an adequate diameter and sufficient column and tensile strengths desirable for manipulating the flexible distal end of the device.

In FIG. 7D, extension of the delivery lumen tube 56 beyond the end of the inflation lumen 42 allows remote manipulation of the catheter's distal end 65 if the push-pull wire 62 is attached to the catheter using, e.g., markers or platinum bands 67. The delivery tube lumen 56 may be made of any of the above materials with respect to tube 26 in FIG. 6.

Figure 8A:
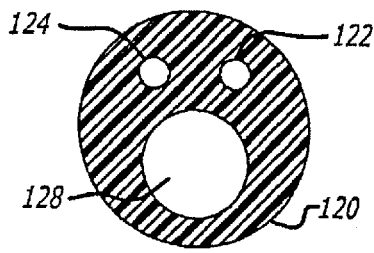
Figure 8B:
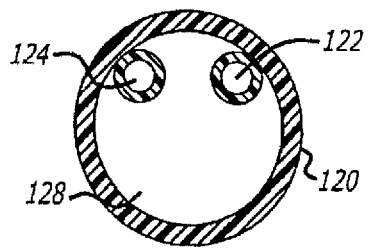

Some of the various configurations of the catheter's lumina (e.g., inflation, push-pull, delivery, etc.) are displayed in FIGS. 8A through 8I1. In FIG. 8A, the optional inflation lumen 122 and push-pull wire lumen 124 are formed interior to the catheter wall 120, while the interior catheter wall forms the guidewire lumen 128. In FIG. 8B, the catheter wall 120 forms the guidewire lumen 128 that includes the optional inflation lumen 122 and push-pull wire lumen 124. The optional inflation lumen 122 is formed interior to the catheter wall 120 of FIG. 8C, while the push-pull wire lumen 124 lies within the larger coil lumen 128 (which is formed by the catheter wall 120).

Figure 8C:
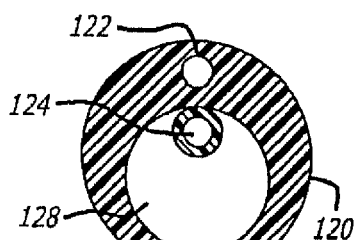
Figure 8D:
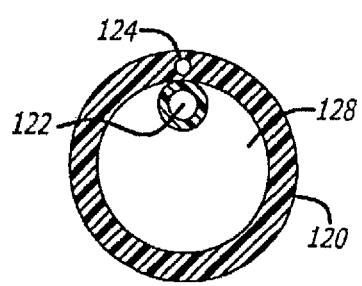
Figure 8E:
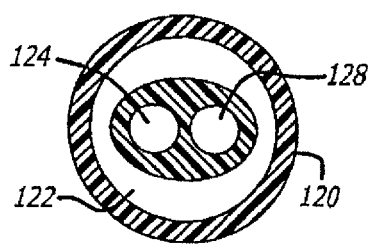
Figure 8F:
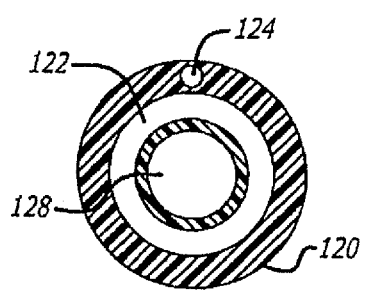
Figure 8G:
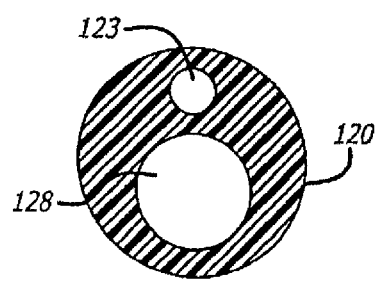
Figure 8H:
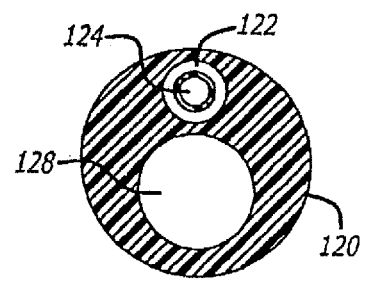

FIG. 8D is a variation of FIG. 8C in which the push-pull wire lumen 124 lies interior to the catheter wall 128 while the optional inflation lumen 122 lies within the larger main lumen 128. In FIG. 8E, the interior catheter wall 120 forms the optional inflation lumen 122, and the push-pull wire lumen 124 and the main lumen 128 are found within the inflation lumen 122. The optional inflation lumen 122 surrounds the guidewire lumen 128 and lies within the region formed interior catheter wall 120 in FIG. 8F, while the push-pull wire lumen 124 lies within the catheter wall 120. In FIG. 8G, one shared lumen 123 serves as the push-pull and optional inflation lumen; the shared push-pull and inflation lumen 123 along with the guidewire lumen 128 lie within the catheter wall 120. Another alternate variation of the lumina positioning, shown in FIG. 8I1, has the push-pull wire lumen 124 lying interior to the inflation lumen 122 which is included within the catheter wall 120, while a separate lumina for the guidewire 128 also is included within the catheter wall.

The tube constructions, hinge region construction, and other tubing forming the various lumina discussed herein may be created through extrusion, sequential production (in which the parts are manufactured separately and later assembled together), or some other method. Moreover, if use of the balloon is omitted from the catheter assembly, the inflation lumen may be omitted entirely as well.

FIG. 9A shows a cross-sectional side view of another variation of a catheter assembly 210. This embodiment includes a catheter body 212 with a main lumen 216 defined through the length of the assembly 210. The push-pull wire lumen 214 may also be defined through the length of the catheter body 212, or at least through a majority of the length of catheter body 212, extending from a fitting 232 at a proximal end of the catheter assembly 210 to a region near or at the distal end of the device. The catheter body 212 may comprise several regions, each having a different degree of flexibility. For instance, the catheter assembly 210 may comprise a first portion 220 distal of the fitting 232 having a first stiffness. A second portion 222, having a second stiffness and located distal of the first portion 220, may be more flexible relative to the first portion 220. Likewise, a third portion 224, having a third stiffness and located distal of the second portion 222, may be more flexible relative to the first and second portions 220, 222, respectively. Thus, the catheter body 212 may have a length comprising progressively more flexible sections that are farther distally located along the catheter 212. Bending portion or flexible joint region 218 may be positioned distal to the third section 224, as described in further detail below.

The push-pull wire lumen 214 is reinforced along at least a substantial portion of its length. The wire lumen 214 may include a braided ribbon 236 integrated throughout the length of lumen 214 along catheter body length 226. Alternatively, the braided ribbon 236 may be integrated through lumen 214 to terminate proximally of joint region 218, as shown in the FIG. 9A. The braided ribbon 236 may be a uniform braid or it may be braided with a varying braid pitch. For instance, proximal sections of the catheter body 212, such as first portion 220, may have a braid which is tighter or which has a higher braid pitch than more distally located sections, such as third portion 224. When a region of lower braid pitch is flanked by regions of higher braid pitch, the region of greater pitch may generally be stiffer during manipulation of the distal catheter tip.

The braided ribbon 236 may be made from a number of materials. For instance, the braided ribbon 236 of an embodiment includes metals which are members of a class of alloys know as super-elastic alloys. Example super-elastic alloys include the class of nickel-titanium materials typically known as Nitinol. Other appropriate metals may also be used, such as stainless steel or polymers may also be used such as liquid crystal polymers (LCPs). The braids of an embodiment are made using commercially available tubular braiders. The term "braid" may generally include tubular constructions in which the ribbons making up the construction may be woven radially in an in-and-out fashion as they cross to form a tubular member defining a single lumen. Other braiding variations may also be used. The braid may also be made from a suitable number of ribbons or wires. FIG. 9D shows a cross-section of catheter body 212. As shown, wire lumen 214 may have a liner 246, e.g., a lubricious polymeric liner, such as polytetrafluoroethylene (PTFE), available commercially under the trade name "TEFLON," for example, disposed upon the lumen wall to facilitate movement of a push-pull wire of the lumen. The liner 246 may be made from any variety of suitable polymeric materials as described herein. Alternatively, the braided ribbon 236 may be positioned upon the inner surface of wire lumen 214. In such a configuration, a lubricious coating may be optionally omitted from the distally located portions of the device.

Although three sections of variable stiffness are described in embodiments, this is intended to be illustrative. Catheters having as few as two sections or multiple (e.g., more than two) sections of variable stiffness are also within the scope of the embodiments described herein. Furthermore, although the sections of an embodiment have decreasing stiffness (or greater flexibility) distally along the catheter body 212, other variations may include distally located sections with increasing stiffness or alternating sections of relatively stiffer and more flexible sections, or any other combinations.

First portion 220 may, for example in one variation, have a typical length of about 100 centimeters (cm) (+/−1 cm) with a stiffness or relative durometer hardness value of 72 D. The second portion 222 may have a length of about 30 cm (+/−1 cm) with a lower stiffness or hardness of 63 D. Third portion 224 may likewise have a length of about 30 cm (+/−1 cm) with an even lower stiffness or hardness value of 40 D. In either case, the main lumen 216 may be defined by tubing having a stiffness or relative hardness of, e.g., 63 D, encased throughout the length of the device. Each of the sections is integral with adjacent sections. The variable stiffness may be effected through one of any variety of methods, e.g., different sheaths or coverings having differing stiffness. For instance, PEBAX (Atochem Corporation of France) or any other polymeric material mentioned above, having the variable stiffness may be used to cover the respective sections.

The manipulatable or flexible joint region 218 is generally located at the distal end of the catheter body 212 and is configured to bend when manipulated by the push-pull wire. Flexible joint region 218 may be configured to have a length ranging from, e.g., approximately 3 mm to 3 cm. As described herein, the braided ribbon 236 may terminate proximally of the flexible joint region 218. The bending portion 218 may be varied to extend to where braid 236 terminates, or it may be extended to bending portion 228 to encompass a portion of the braid 236. The flexible joint region 218 may be covered by PEBAX, or any other polymeric material mentioned above, having a stiffness or hardness of, e.g., 25 D, which is lower than a stiffness of third portion 224.

As mentioned above, the proximal portion of the catheter body 212 of an embodiment is attached to fitting 232. Fitting 232 may be any variety of fitting typically utilized with intra-luminal catheters. In this variation, fitting 232 may define an opening 234 which is in communication with main lumen 216 to allow for the passage of guidewires, various tools, therapeutic drugs, etc. It may also be configured to accept a separately manufactured push-pull wire handle 238 with a control 240 for manipulating the push-pull wire distally or proximally along a longitudinal axis of the wire. Alternatively, the push-pull wire handle 238 may be formed as an integrated piece with fitting 232. Although the figure shows the inclusion of opening 234 in the proximal end of fitting 232, other variations may include rapid-exchange (RX) type catheter designs having guidewire lumen openings defined along the body of catheter body 212.

The distal end of flexible joint region 218 may have a portion of the tubing defining the main lumen 216 extending as an extension 230 past distal face 242 of joint region 218, as shown in the detail side view of FIG. 9B. The length of extension 230 may be configured to extend at various lengths from a relatively short length to a relatively longer length, depending upon the desired bending results. Extension 230 may have a relative stiffness or hardness value, e.g., 63 D, which is higher than the stiffness or hardness of the section located proximally, i.e., flexible joint region 218. Moreover, an additional coating may be disposed over extension 230 and any marker bands or wires positioned thereon to encase the assembly, as described in detail herein. An end view of flexible joint region 218 is shown in FIG. 9C, which illustrates the variation of the push-pull wire lumen 214 formed adjacent to main lumen 216. As shown, main lumen 216 may have a lubricious liner 244, such as polytetrafluoroethylene (PTFE), available commercially under the trade name "TEFLON," for example, defined upon an inner surface of main lumen 216 to facilitate the insertion or removal of guidewires and/or other tools through the main lumen 216. Liner 244 may be formed from any variety of suitable polymeric materials, as described above.

The central and push-pull lumens of embodiments described herein are circular (e.g., FIGS. 3, 9C, 9D, etc.). Upon activation of the push-pull wire into the push position, for example, the distal end deflects (e.g., FIG. 4), causing the push-pull wire lumen to change shape from circular to oval. This ovalization results in a minor axis that is less the diameter of the circular push-pull wire lumen in the neutral or reference position and pinches (compresses) the push-pull wire. As the push-pull wire is activated into the push position, the circular lumen begins to ovalize and compress or pinch the push-pull wire, which can make it relatively more difficult to deflect the catheter while thinning the outer wall of the push-pull lumen.

More specifically, when the push-wire wire is activated from the neutral to the pull position (e.g., FIG. 4), the distal aspect of the catheter flexes or bends at the flexible joint region. The resultant flexion of the flexible joint in the pull position bends the catheter generally about a centroid of the cross section of the catheter, putting the push-pull lumen in compression and shortening it relative to the opposite side of the catheter (which is in tension), causing the outer wall of the push-pull lumen to slightly pleat or have an undulating surface appearance at the bend.

Moreover, when the push-pull wire is activated from the neutral to the push position (e.g., FIG. 4), the distal aspect of the catheter flexes or bends at the flexible joint region and in a direction opposite of the pull position. The flexion of the flexible joint in the push position bends the catheter generally about a centroid of the cross section of the catheter, putting the push-pull lumen in tension and elongating it relative to the opposite side of the catheter (which is in compression), causing the push-pull lumen to ovalize and pinching the push-pull wire and thinning the outer wall of the push-pull lumen.

From the aforementioned, the inherent effects on the cross-sectional shape of the circular push-pull lumen when the push-pull wire is actuated are overcome in an embodiment by configuring the push-pull lumen to have an approximately oval cross-section instead of a circular cross-section. Alternatively, the inherent effects on the cross-sectional shape of the circular push-pull lumen when the push-pull wire is actuated are overcome in an embodiment by configuring the push-pull wire as a flat wire instead of a circular wire. As such, a flat push-pull wire placed in an oval push-pull lumen is a relatively more efficient design that increases the flexion of the flexible joint, reduces the push-pull force to actuate the push-pull wire, and prevents rupture of the outer wall of the push-pull lumen causing the push-pull wire to exit the ruptured wall.

Figure 10A:
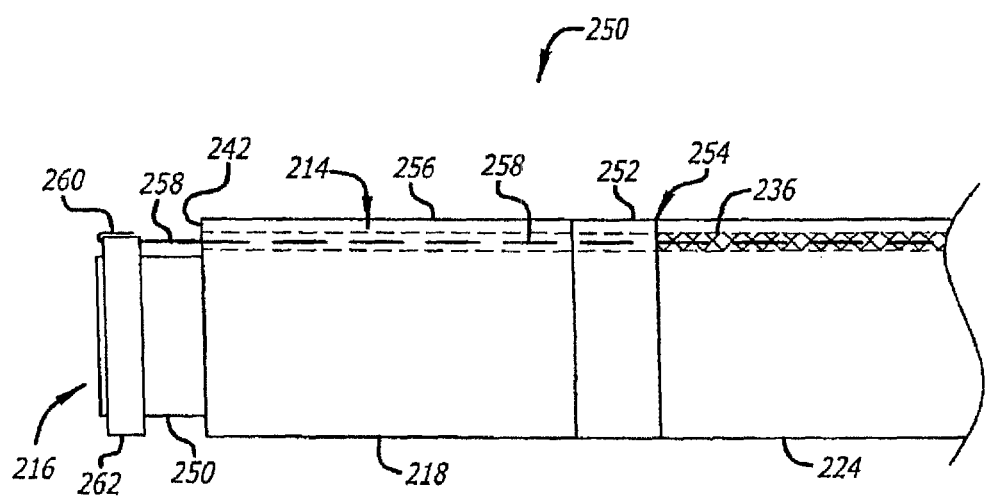
FIG. 10A shows an assembly side view of the distal portion of a variation of the catheter assembly, under an embodiment.

Returning to FIG. 9B, tubing extension 230 may extend for a short distance past distal face 242, for instance, approximately 0.15 cm. As shown in the side view of distal portion 250 in FIG. 10A, a radio-opaque marker band 262, as described herein, may be attached over and/or onto extension 230. The push-pull wire 258 positioned within wire lumen 214 may extend through an opening in distal face 242 and attach to marker band 262. Push-pull wire 258 may be attached via a routing between band 262 and extension 230 and bent around 260 marker band 262. Alternatively, additional marker bands may be positioned upon extension 230 and used to sandwich the push-pull wire 258 between the respective marker bands. Other variations for attaching the wire 258 to the marker band 262 may also be used. The portion of extension 230 past marker band 262 may be left or it may alternatively be trimmed flush against the marker band 262. An additional marker band may be positioned about the push-pull wire lumen 214 to aid in positional orientation of the catheter under an imaging system, such as a fluoroscope.

The flexible joint region 218 may flex beginning where braiding 236 terminates 254. Flexible joint region 218 may also incorporate an optional transitional joint region 252 between the flexible joint region 218 and the remainder of the catheter body. This transition region 252 may have an intermediate flexibility between that of joint region 218 and the catheter body or it may be configured to be more flexible than either region to facilitate bending of the region. Flexibility may be imparted to region 252, at least in part, by omitting any liners or coatings from the main lumen 216 and/or the wire lumen 214 along the region 252. In either case, the transition region 252 may be omitted entirely. The covering or sheath 256, which is hydrophilic and may be disposed over the entire device or portions of the device, may also be omitted from the flexible joint region 218. This covering 256 may also be included or omitted entirely from the transitional joint region 252, depending upon the desired results. Optionally, the distal portion of the device (optionally including the joint region 252), perhaps approximately 35 to 50 cm, may be covered with the hydrophilic coating, again depending upon the desired results.

Figure 10B:
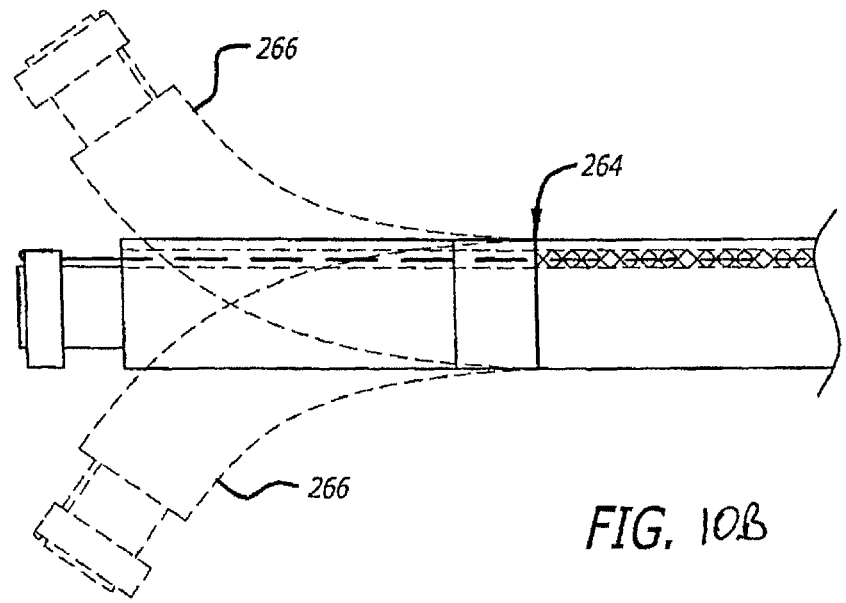
FIGS. 10B and 10C show bending of the flexible joint regions of catheters having differing lengths of the flexible joint regions, under an embodiment.
Figure 10C:
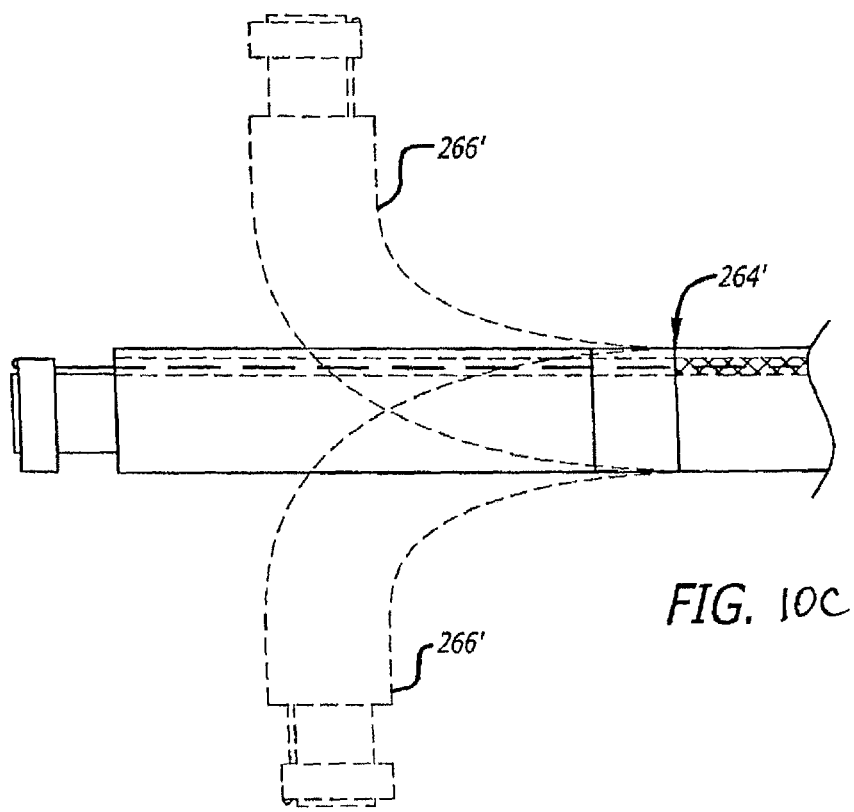

By varying the length of flexible joint region 218, the amount of curvature and flexure of the joint region 218 can be controlled. For instance, a joint region having a relatively shortened length between the distal end of the joint region 218 and the terminal end 264 of the braid, as shown in FIG. 10B, may allow for a reduced degree of flexure 266 relative to a neutral position of the catheter. In comparison, as shown in FIG. 10C, a lengthened joint region extending to a more proximally located terminal end 264' may allow for a relatively greater degree of flexure 266' relative to the flexure shown by the catheter in FIG. 10B. Accordingly, the degree of flexure may be controlled in part by the length of the flexible joint region. Thus, the flexible region may be flexed up to 90 degrees relative to the longitudinal axis of the catheter assembly, and in some cases the flexible region may be flexed up to 180 degrees relative to the longitudinal axis depending upon the length of the flexible joint region. To further facilitate bending of the catheter, additional members such as coils may be incorporated into the device, for instance in the transitional region, to aid in further controlling the bending of the joint region.

Figure 11A:
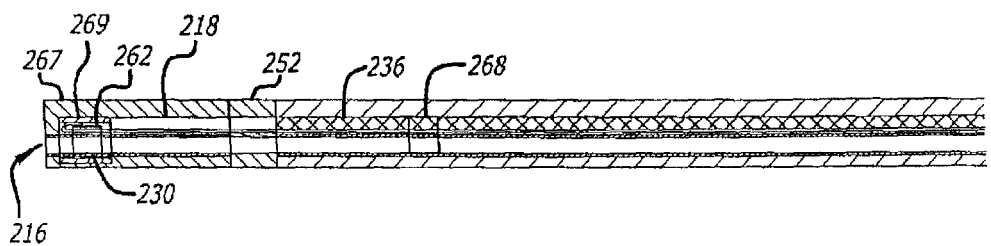
FIGS. 11A and 11B show cross-sectional side and detail side views, respectively, of another variation of the device where the distal end may be fused down by a liner, under an embodiment.
Figure 11B:
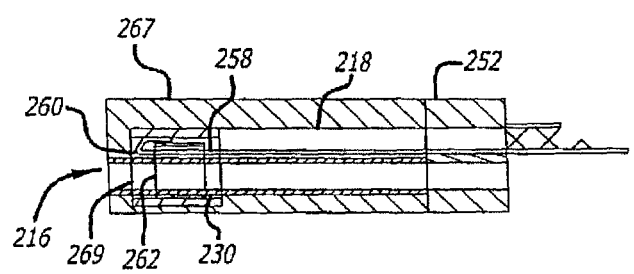

As mentioned above, the distal flexible joint region 218 may have a coating or liner 267, for example one that is hydrophilic for ease of use within a body, disposed over it and over extension 230 to encase the assembly, as shown in the cross-sectional side view of FIG. 11A. In this variation, marker band 262 may be disposed over the extension 230 and a second marker band 269 may be disposed thereupon with the push-pull wire 258 locked in between. In this variation, second marker band 269 is larger in diameter as well as length than marker band 262; however, other sizes and configurations may be used. The liner 267, which may be fused down over the entire length of the joint region 218 or just a portion of the region 218, may be made of any variety of materials described herein. The marker bands 262, 269 may be utilized to facilitate visualization of a position of the distal end of the device. Optionally, a third marker band 268 may be positioned along the device proximal to the joint region 218 to aid in visualizing potential coiling of the device.

In order to control the advancement or retraction of the push-pull wire, which controls the flexure of the flexible joint region, a variety of controls may be utilized. FIGS. 12A to 12C show side, end, and partially removed side views, respectively, of one variation of a control handle. A push-pull wire guide 270 may extend from handle 238 for transitioning the push-pull wire to the catheter. As shown in the side view of FIG. 12C, which shows handle 238 partially removed for clarity, wire control 240 is configured as a wheel which further defines a concentrically configured gear 272, as shown in FIG. 12D, which may engage with the engagement teeth 276 of rack 274, as shown in FIG. 12E. The push-pull wire may be attached to the rack 274 so that as control 240 is rotated, rack 274 may be advanced proximally or distally to thereby translate the attached push-pull wire along the longitudinal axis of the wire.

Figure 13:
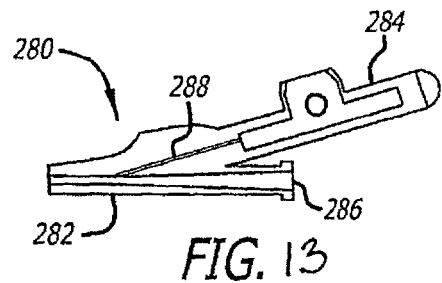
FIG. 13 shows another variation in the cross-sectional side view of combination fitting/handle assembly, under an embodiment.
Figure 14:
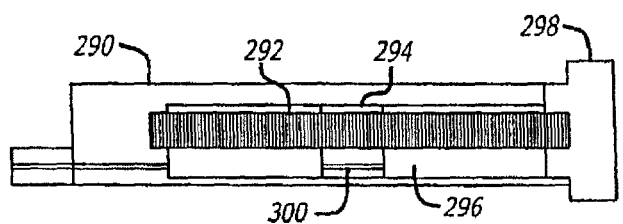
FIG. 14 shows another variation in the cross-sectional side view of the handle body utilizing a carriage screw, under an embodiment.

FIG. 13 shows another variation in the cross-sectional side view of combination fitting/handle assembly 280. Handle body 282 may incorporate the push-pull handle portion 284 as an integrated part of a fitting. The assembly 280 may include a main lumen access 286 as well as a push-pull wire access 288. FIG. 13 shows a cross-sectional side view of another variation in handle body 290. In this variation, a carriage screw 292 may be positioned within the handle 290 such that a wire carriage 294 is configured to travel within advancement channel 296 defined within handle 290. A proximal end of carriage screw 292 may be attached to a control knob 298, which may be rotated to advance either proximally or distally the carriage 294 and the push-pull wire, which may be attached to carriage 294 at push-pull wire attachment 300.

Figure 15:
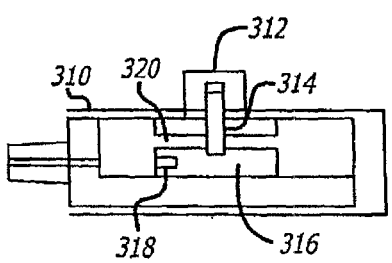
FIG. 15 shows another variation in the cross-sectional side view of the handle body utilizing a control/release knob, under an embodiment.
Figure 16:
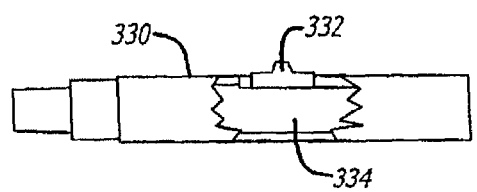
FIG. 16 shows another variation in the cross-sectional side view of the handle body utilizing a control slide, under an embodiment.

In yet another variation in FIG. 15, handle body 310 may incorporate a control/release knob 312 which is attached to a release screw 314. The screw 314 may be attached to a wire carriage 316, which may attach to push-pull wire via attachment 318. As the knob 312 is translated proximally or distally, carriage 316 may travel within channel 320 to either advance or retract the attached push-pull wire. Knob 312 may be tightened about screw 314 against handle 310 to lock a position of the push-pull wire during flexure, if desired. In yet another variation in FIG. 16, handle body 330 may have a control slide 332 configured to proximally or distally advance a wire carriage 334 within handle 330.

Figure 17:
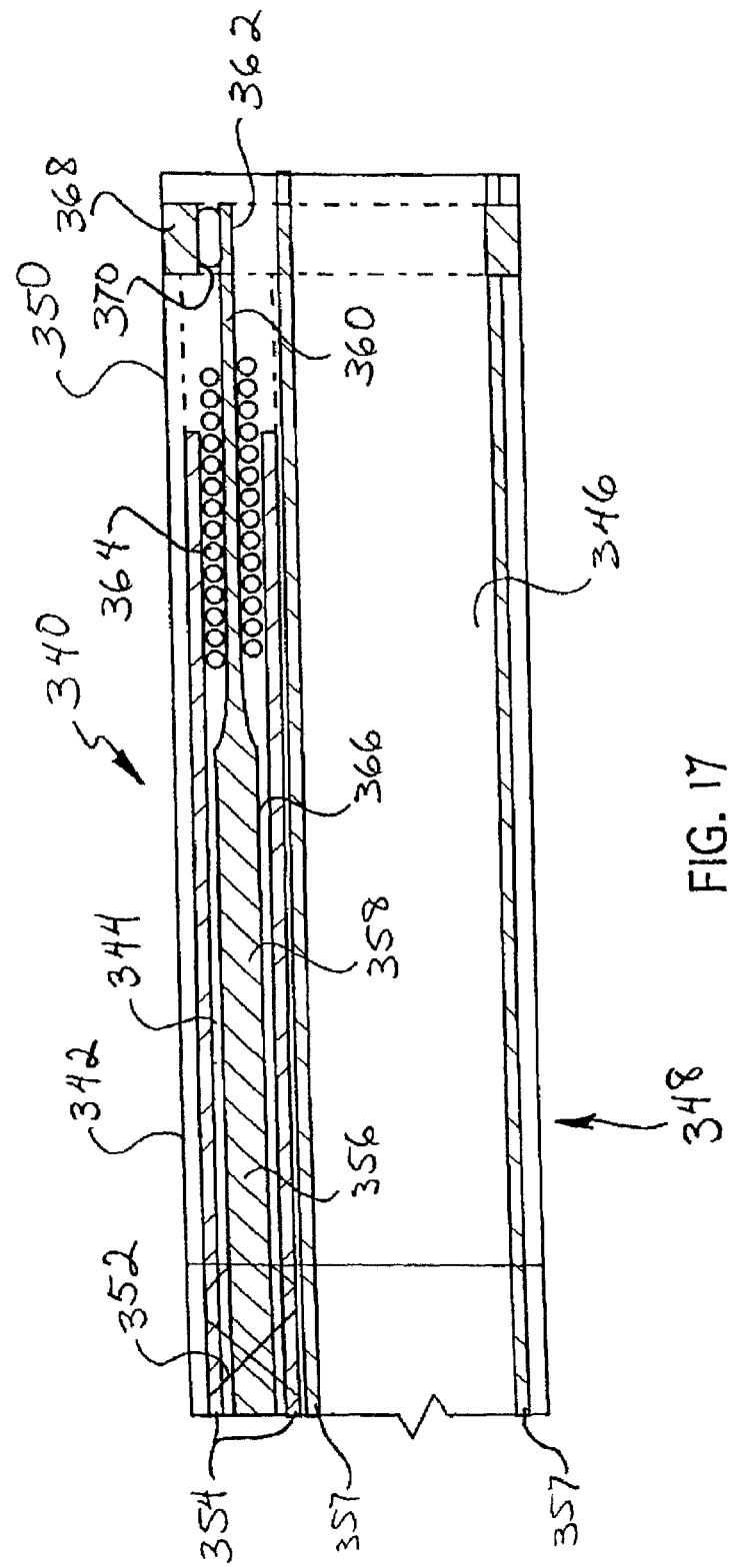
FIG. 17 is a cross-sectional view of another variation of the distal region of the catheter assembly including a coil over a distal portion of the push-pull wire, under an embodiment.
Figure 18:
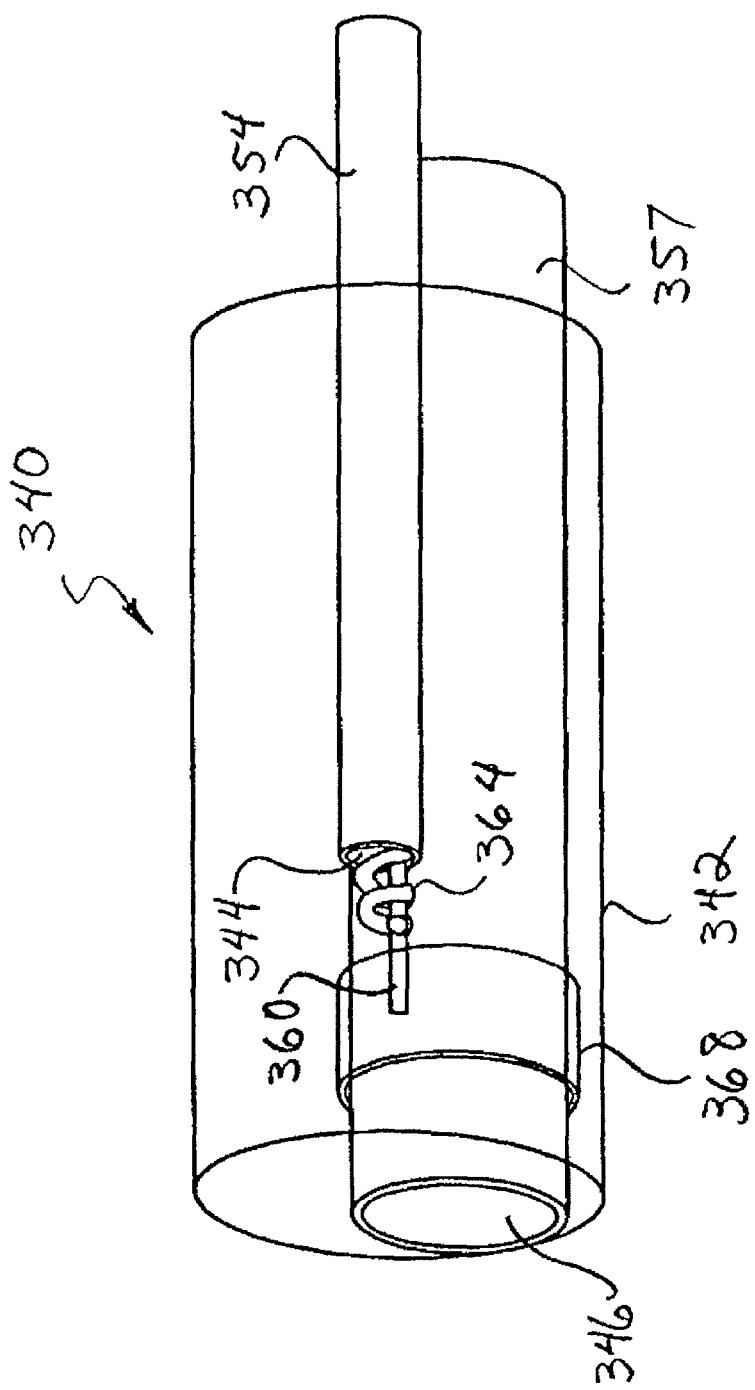
FIG. 18 is a perspective diagrammatic view illustrating the variation of the distal region of the catheter assembly including a coil over a distal portion of the push-pull wire, under an embodiment.

FIGS. 17 and 18 illustrate another variation of a catheter assembly 340, having a catheter body 342 with a main lumen 346 defined through the length of the catheter assembly. The push-pull wire lumen 344 may also be defined through the length of the catheter body, or at least through a majority of the length of catheter body, extending from a fitting (not shown) at a proximal end of the catheter assembly to a region near or at the distal end of the device. The catheter body itself may comprise several regions, each having a different degree of flexibility. Bending portion or flexible joint region 348 may be positioned at a distal section 350 of the catheter assembly.

The push-pull wire lumen is reinforced along at least a substantial portion of its length, and, as described above, may include a braided ribbon 352 integrated throughout the length of push-pull wire lumen along catheter body length, to terminate proximally of the flexible joint region. The push-pull wire lumen may have a liner 354, e.g., a lubricious polymeric liner, disposed upon the lumen wall to facilitate movement of the push-pull wire 356 in the lumen. The lubricious polymeric liner may be formed of a material with a low coefficient of friction, such as polytetrafluoroethylene (PTFE), for example, available commercially under the trade name "TEFLON," although other similar materials with a low coefficient of friction, such as polyethylene or polypropylene, for example, are also suitable, and the liner may be made from any variety of suitable polymeric materials such as are described above. The main lumen may also have such a lubricious liner 357. The push-pull wire is a tapered wire which has a larger diameter portion 358 along a proximal portion and a smaller diameter distal portion 360 at or near its distal end 362, and may be fabricated from a biocompatible metallic material such as stainless steel, platinum, and the like. A coil 364 is placed around the smaller diameter portion, typically approximately 6 cm at the end of an 8 cm long catheter, so that the tip of the push-pull wire does not deflect and rupture the otherwise constant diameter catheter. The coil has the effect of distributing stress along the smaller diameter portion of the push-pull wire to prevent buckling of the smaller diameter portion of the push-pull wire. The push-pull wire is also preferably coated with a material 366 with a low coefficient of friction, such as polytetrafluoroethylene, for example, available commercially under the trade name "TEFLON," although other similar materials with a low coefficient of friction, such as polyethylene or polypropylene, for example, may also be suitable.

A radio-opaque marker band 368, as described above, may be attached over and/or onto the catheter body at or near the distal section of the catheter assembly. The push-pull wire positioned within the push-pull wire lumen may attach to the marker band, such as by welding the distal end of the push-pull wire to a radially inner surface 370 of the marker band, for example, although the push-pull wire may be attached at its distal end to the catheter through a variety of methods, e.g., adhesives, crimping, mechanical fasteners, and the like. An additional marker band may be positioned about the push-pull wire lumen to aid in positional orientation of the catheter under an imaging system, such as a fluoroscope.

Figure 19:
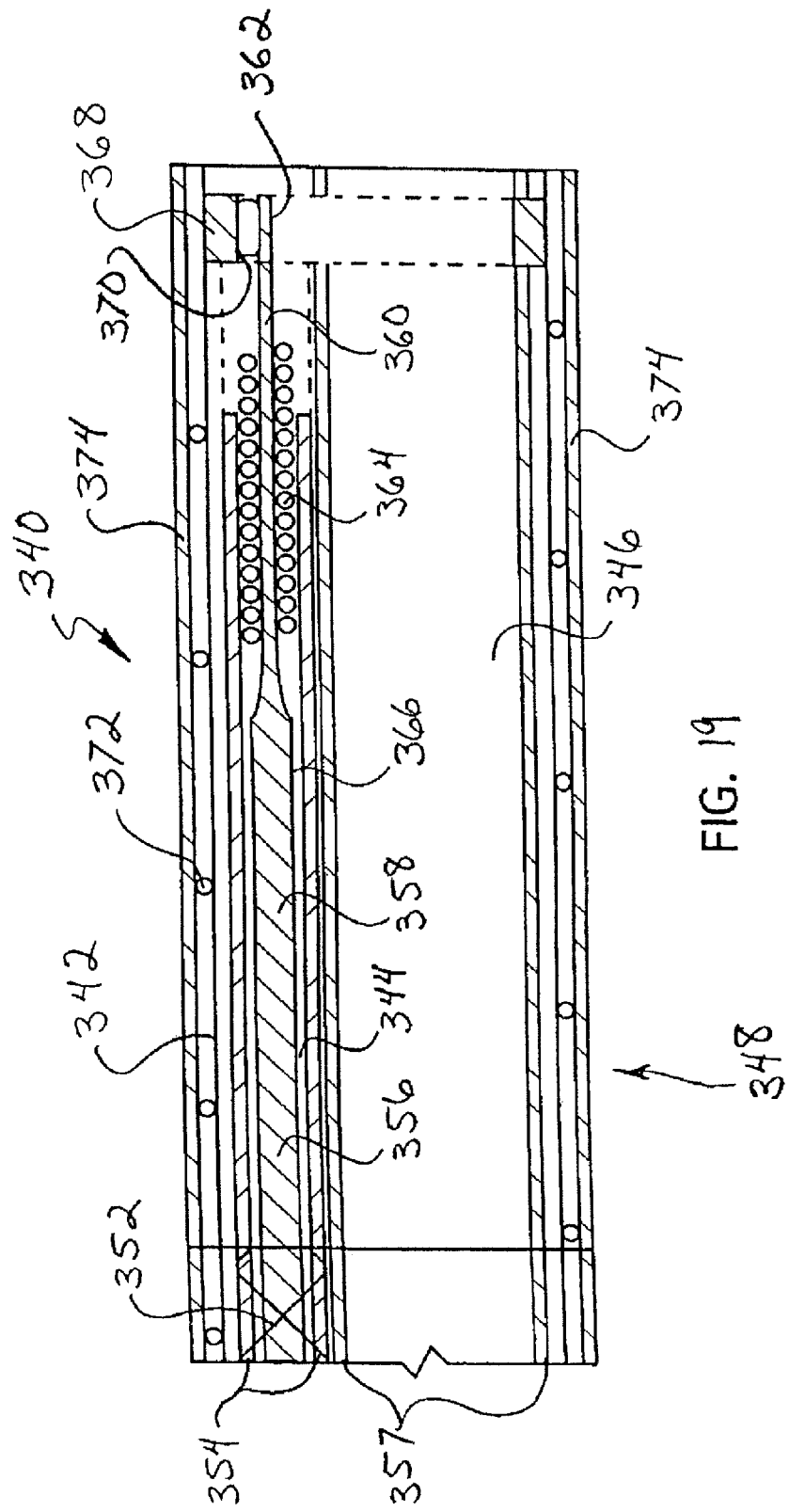
FIG. 19 is a cross-sectional view of another variation of the distal region of the catheter assembly including a strapping coil over a distal portion of the catheter body, under an embodiment.
Figure 20:
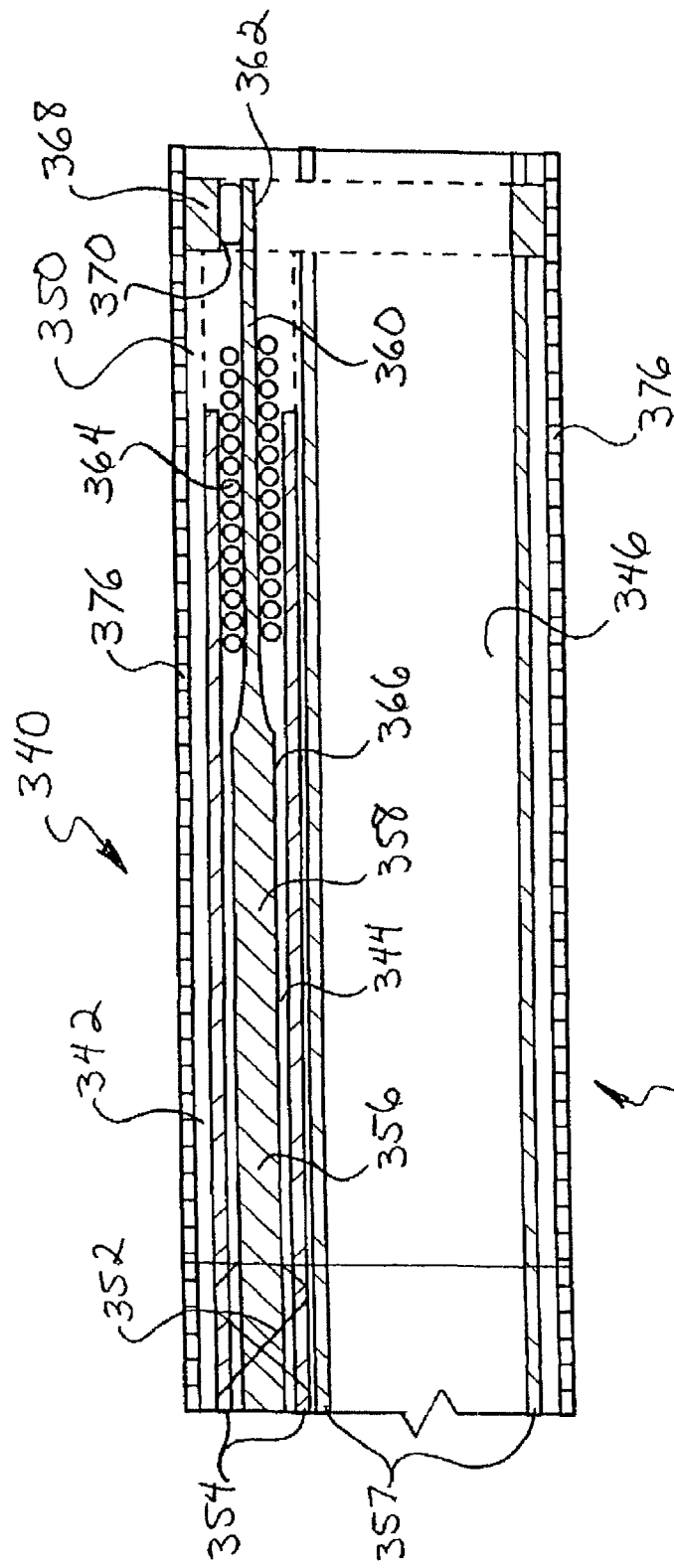
FIG. 20 is a cross-sectional view of another variation of the distal region of the catheter assembly including a mesh over a distal portion of the catheter body, under an embodiment.
Figure 21:
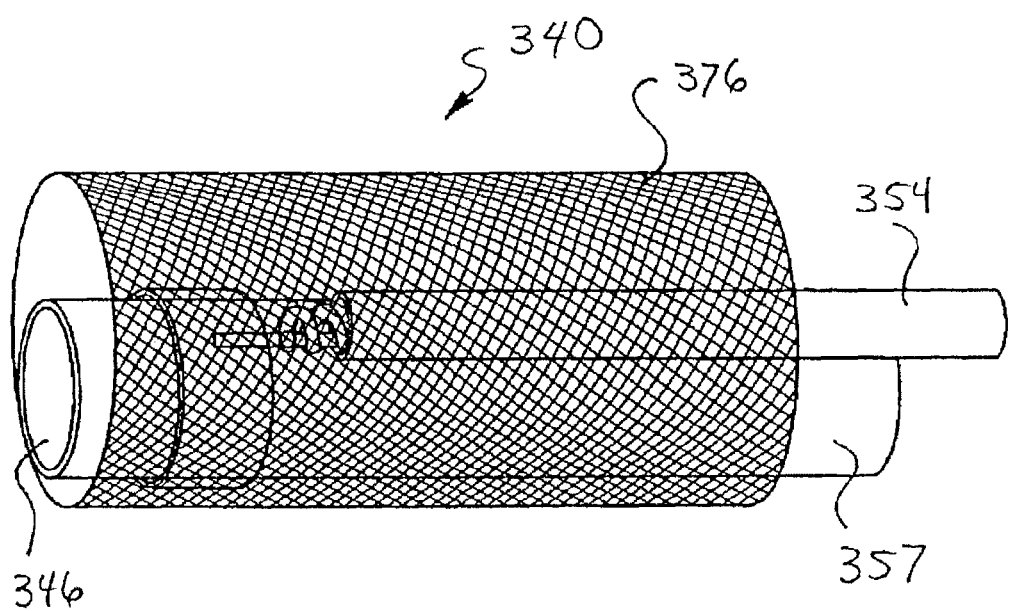
FIG. 21 is a perspective diagrammatic view showing the variation of the distal region of the catheter assembly including a mesh over a distal portion of the catheter body, under an embodiment.

In another variation shown in FIG. 19, a strapping coil 372 may also be placed around the outside of the catheter to prevent the catheter from rupturing if the push-pull wire buckles when the push-pull wire is pushed. The strapping coil may be covered by an outer covering 374 formed of a polymeric material, such as of PEBAX, for example, as described herein. In another variation illustrated in FIGS. 20 and 21, an outer covering 376 of a very fine mesh formed of a polymeric material, such as polyethylene terephthalate (PET), for example, may be placed over the distal tip of the catheter to prevent rupture of the lumen and reinforce the push-pull wire.

The applications of the catheter described herein are not limited to certain treatments, but may include any number of vascular maladies. Modification of the above-described methods for carrying out the embodiments, and variations of the mechanical aspects of the embodiments that are obvious to those of skill in the mechanical and guide wire and/or catheter arts are intended to be within the scope of the claims. Moreover, various combinations of aspects between examples are also contemplated and are considered to be within the scope of this disclosure.

Embodiments described herein include a catheter or catheter section used for negotiating movement along small-diameter, tortuous vessels. The catheter may comprise a flexible joint region which defines a main lumen and an adjacent wire lumen, the wire lumen having an opening near or at a distal end of the flexible joint region; a push-pull wire configured to be pushed or pulled along a longitudinal axis of the wire through the wire lumen; and wherein the flexible joint region has a predetermined length sized to affect a flexure of the flexible joint region. Moreover, the catheter assembly may further comprise at least one radio-opaque marker band near or at the distal end of the flexible joint region for securing the push-pull wire thereto, wherein the flexible joint region has a predetermined length sized to affect a flexure of the flexible joint region.

An inflatable balloon member may optionally be used with the catheter assembly. If the inflatable member is utilized, the flexible joint may variously be distal of the inflatable member, within the inflatable member, or proximal of the inflatable member.

One particular variation of the catheter assembly may have a catheter body that defines a main lumen through the length of the assembly. A push-pull wire lumen having an open distal end may also be defined through the length of the catheter body, or at least through a majority of the length of catheter body, extending from a fitting at a proximal end of the catheter assembly to a region near or at the distal end of the device. The catheter body itself may be comprised of several regions each having a different degree of flexibility. For instance, the catheter assembly may comprise a first portion distal of the fitting having a first stiffness. A second portion, having a second stiffness and located distal of the first portion, may be more flexible relative to the first portion. Likewise, a third portion, having a third stiffness and located distal of the second portion, may be more flexible relative to the first and second portions. Thus, the catheter body may have a length comprised of progressively more flexible sections the farther distally located along the catheter. Distal to the third section, bending portion or flexible joint region may be positioned, as described in detail herein.

The push-pull wire lumen may include a braided ribbon integrated throughout the length of the lumen. Alternatively, the braided ribbon may be integrated through the lumen to terminate proximally of the joint region. The braided ribbon may be a uniform braid or it may be braided with a varying braid pitch. The braided ribbon may be made from a number of materials. For example, metals that are members of a class of alloys known as super-elastic alloys are used for the braid material of an embodiment, but are not so limited.

The manipulatable or flexible joint region is generally located at the distal end of the catheter body and is configured to bend when manipulated by the push-pull wire. The bending portion itself may be varied to extend to where the braid terminates, or it may be extended to the bending portion to encompass a portion of the braid. By varying the length of the flexible joint region, the amount of curvature and flexure of the joint region can be controlled. For instance, a joint region having a relatively shortened length between the distal end of the joint region and the terminal end of the braid may allow for a reduced degree of flexure relative to a neutral position of the catheter. In comparison, a lengthened joint region extending to a more proximally located terminal end may allow for a relatively greater degree of flexure. Accordingly, the degree of flexure may be controlled in part by the length of the flexible joint region. Thus, the flexible region may be flexed up to 90 degrees relative to the longitudinal axis of the catheter assembly and in some cases, the flexible region may be flexed up to 180 degrees relative to the longitudinal axis depending upon the length of the flexible joint region. To further facilitate bending of the catheter, additional members such as coils may be incorporated into the device, for instance in the transitional region, to aid in further controlling the bending of the joint region.

In another embodiment, the catheter section includes a tubing extension extending distally from the main lumen of the distal end of the flexible joint region. In an embodiment, the radio-opaque marker band may be attached to the tubing extension. The push-pull wire typically extends through the opening of the wire lumen at the distal end of the flexible joint region, and may be attached to the marker band attached to the tubing extension.

In another embodiment, the catheter section includes a control in communication with a proximal end of the push-pull wire for manipulating the flexible joint region. The control typically includes a handle receiving the proximal end of the push-pull wire; and a wire control member mounted to the handle and engaging the push-pull wire, whereby movement of the wire control member translates the push-pull wire along the longitudinal axis of the push-pull wire. In one presently preferred aspect, the handle includes a push-pull wire guide extending from the handle, and the push-pull wire passes through the push-pull wire guide for transitioning the push-pull wire to the catheter body. In another presently preferred aspect, the handle is integrated into a catheter fitting connected to the catheter body, the catheter fitting including a main lumen access and a push-pull wire access.

In another embodiment, the proximal end of the push-pull wire is attached to a rack bearing a plurality of engagement teeth, and the wire control member engaging the engagement teeth of the rack, such that movement of the wire control member advances the rack proximally or distally to thereby translate the attached push-pull wire along the longitudinal axis of the push-pull wire. In an embodiment, the wire control member includes a wheel defining a concentrically configured gear engaging the engagement teeth of the rack, whereby rotation of the wheel advances the rack proximally or distally to thereby translate the push-pull wire along the longitudinal axis of the push-pull wire.

In another embodiment, the proximal end of the push-pull wire is attached to a wire carriage, and the wire control member includes a carriage screw disposed within the handle, the wire carriage being configured to travel within an advancement channel defined within the handle, and a proximal end of the carriage screw being attached to a control knob that may be rotated to advance the wire carriage and the push-pull wire either proximally or distally along the longitudinal axis of the push-pull wire.

In another embodiment, the proximal end of the push-pull wire is attached to a wire carriage, and the handle comprises a control release knob attached to a release screw attached to the wire carriage, whereby the control release knob may be translated proximally or distally such that the wire carriage travels within an advancement channel to advance or retract the push-pull wire. In an embodiment, the control release knob may be tightened about the release screw against the handle to lock a position of the push-pull wire.

In another embodiment, the proximal end of the push-pull wire is attached to a wire carriage, and wherein the wire control member comprises a control slide configured to proximally or distally advance the wire carriage within the handle to thereby translate the push-pull wire along the longitudinal axis of the push-pull wire.

Another embodiment provides for a catheter section including a catheter body having a proximal end and a distal end, the catheter body including a distal flexible joint region, a main lumen extending through the catheter body and through the flexible joint region, and a wire lumen adjacent to the main lumen and extending through the catheter body and through the flexible joint region. The wire lumen of the flexible joint region has an opening near or at a distal end of the flexible joint region, and a tapered push-pull wire is provided, having a proximal portion of a first diameter and a distal portion of a smaller diameter than the first diameter. The push-pull wire is configured to be pushed or pulled along a longitudinal axis of the wire through the wire lumen, and the distal end of the push-pull wire is attached to the distal flexible joint region. In an embodiment, a coating of a material with a low coefficient of friction is disposed over the push-pull wire.

A coil is also disposed around the smaller diameter distal portion of the push-pull wire, which has the effect of distributing stress along the smaller diameter portion of the push-pull wire to prevent buckling of the smaller diameter portion of the push-pull wire, so that the tip of the push-pull wire does not deflect and rupture the catheter body. A control is also provided in communication with a proximal end of the push-pull wire for manipulating the flexible joint region.

In another embodiment, a strapping coil is disposed around the outside of the catheter, and an outer covering formed of a polymeric material, such as PEBAX, for example, may be disposed around the strapping coil. In another variation, an outer covering of a mesh formed of a polymeric material, such as polyethylene terephthalate, for example, may be disposed around the distal tip of the catheter. In another embodiment, at least one radio-opaque band may be mounted to the catheter body near or at the distal end of the flexible joint region, the push-pull wire extends through the opening of the wire lumen at the distal end of the flexible joint region, and push-pull wire is attached to the marker band. In another presently preferred aspect, the wire lumen further comprises a braid along at least a substantial portion of the wire lumen, and typically the braid terminates proximally of the flexible joint region. In another embodiment, the main lumen includes a lining, such as a lubricious lining, for example, along at least a substantial portion of the main lumen. The wire lumen may also be provided with a lining, such as a lubricious lining, for example, along at least a substantial portion of the wire lumen.

Embodiments described herein include a device comprising a catheter section including a flexible joint region disposed between a distal end and a proximal end. The device includes a laser fiber disposed within the catheter section. The laser fiber emits laser light at a fiber distal end. The device includes a wire comprising a distal end coupled to the catheter section. The wire is configured to move the distal end of the catheter section from a first position to a second position about the flexible joint region.

Embodiments described herein include a device comprising: a catheter section comprising a flexible joint region disposed between a distal end and a proximal end; a laser fiber disposed within the catheter section, wherein the laser fiber emits laser light at a fiber distal end; and a wire comprising a distal end coupled to the catheter section, wherein the wire is configured to move the distal end of the catheter section from a first position to a second position about the flexible joint region.

The device of an embodiment comprises a first lumen disposed within the catheter section, wherein the first lumen comprises an open distal end at the proximal end of the catheter section, wherein the wire is configured to be pushed and pulled through the first lumen along a longitudinal axis of the wire.

The device of an embodiment comprises a second lumen disposed within the catheter section adjacent the first lumen, wherein the laser fiber is deployed via the second lumen.

The device of an embodiment comprises a guidewire.

The guidewire of an embodiment is deployed via the second lumen.

The device of an embodiment comprises a guidewire lumen disposed within the catheter section adjacent the first lumen, wherein the guidewire is deployed via the guidewire lumen.

The guidewire of an embodiment has at least one of a variable stiffness along its length and a stepped diameter along its length.

The device of an embodiment comprises a radio-opaque band fixed to the catheter section.

The distal end of the wire of an embodiment is secured to the radio-opaque band.

The device of an embodiment comprises an inflatable member.

The flexible joint region of an embodiment is distal of the inflatable member.

The flexible joint region of an embodiment is disposed within the inflatable member.

The flexible joint region of an embodiment is proximal of the inflatable member.

The inflatable member of an embodiment comprises at least one of elastomer, thermoplastic polymer, silicone rubber, latex rubber, natural rubber, butadiene-based co-polymer, EPDM, polyvinyl chloride, complex co-polymer, styrene-ethylene butylene-styrene co-polymer, polyethylene, polypropylene, and Nylon.

The flexible joint region of an embodiment comprises a coil member.

The coil member of an embodiment includes a section comprising a pitch that is larger than adjacent coil pitches.

The flexible joint region of an embodiment comprises a braid.

The braid of an embodiment comprises a section with a pic that is larger than adjacent pics.

The flexible joint region of an embodiment comprises a polymer that is relatively softer than at least one adjacent polymer.

The flexible joint region of an embodiment comprises a wall thickness that is relatively thinner than at least one adjacent wall thickness.

A method comprising forming a catheter section to include a flexible joint region disposed between a distal end and a proximal end. The method comprises housing a laser fiber within the catheter section. The laser fiber emits laser light at a fiber distal end. The method comprises housing a wire in the catheter section and coupling a distal end of the wire to the catheter section. The wire is configured to move the distal end of the catheter section from a first position to a second position about the flexible joint region.

A method comprising: forming a catheter section to include a flexible joint region disposed between a distal end and a proximal end; housing a laser fiber within the catheter section, wherein the laser fiber emits laser light at a fiber distal end; and housing a wire in the catheter section and coupling a distal end of the wire to the catheter section, wherein the wire is configured to move the distal end of the catheter section from a first position to a second position about the flexible joint region.

Embodiments described herein include a catheter section comprising a catheter body having a proximal end and a distal end. The catheter body includes a distal flexible joint region, a main lumen extending through the catheter body and through the flexible joint region, and a wire lumen adjacent to the main lumen and extending through the catheter body and through the flexible joint region. The catheter body defines at least a first region having a first flexibility and a second region having a second flexibility more flexible than the first region. The wire lumen of the flexible joint region has an opening near or at a distal end of the flexible joint region. The flexible joint region has a predetermined length sized to affect a flexure of the flexible joint region. Embodiments include a push-pull wire configured to be pushed or pulled along a longitudinal axis of the wire through the wire lumen. The distal end of the push-pull wire is attached to the distal flexible joint region. Embodiments include a control in communication with a proximal end of the push-pull wire for manipulating the flexible joint region.

Embodiments described herein include a catheter section comprising: a catheter body having a proximal end and a distal end, the catheter body including a distal flexible joint region, a main lumen extending through the catheter body and through the flexible joint region, and a wire lumen adjacent to the main lumen and extending through the catheter body and through the flexible joint region, the catheter body defining at least a first region having a first flexibility and a second region having a second flexibility more flexible than the first region, the wire lumen of the flexible joint region having an opening near or at a distal end of the flexible joint region, wherein the flexible joint region has a predetermined length sized to affect a flexure of the flexible joint region; a push-pull wire configured to be pushed or pulled along a longitudinal axis of the wire through the wire lumen, the distal end of the push-pull wire attached to the distal flexible joint region; a control in communication with a proximal end of the push-pull wire for manipulating the flexible joint region.

The catheter section of an embodiment includes at least one radio-opaque band near or at the distal end of the flexible joint region.

The first region of an embodiment is located distally of the second region.

The second region of an embodiment is located distally of the first region.

The catheter section of an embodiment includes a third region having a third flexibility more flexible than the second region.

The third region of an embodiment is located distally of the second region.

The wire lumen of an embodiment comprises a braid along at least a substantial portion of the wire lumen.

The braid of an embodiment terminates proximally of the flexible joint region.

The main lumen of an embodiment comprises a lining along at least a substantial portion of the main lumen.

The lining of an embodiment comprises a lubricious lining.

The wire lumen of an embodiment comprises a lining along at least a substantial portion of the wire lumen.

The lining of an embodiment comprises a lubricious lining.

The flexible joint region of an embodiment comprises a polymer which is softer than adjacent polymers.

The catheter section of an embodiment includes a coating over at least a majority of the flexible joint region.

The catheter section of an embodiment includes a tubing extension extending distally from the main lumen of the distal end of the flexible joint region.

The catheter section of an embodiment includes a radio-opaque marker band attached to the tubing extension.

The push-pull wire of an embodiment through the opening of the wire lumen at the distal end of the flexible joint region, and is attached to the marker band attached to the tubing extension.

The catheter section of an embodiment includes a radio-opaque marker band positioned about the push-pull wire lumen.

The control of an embodiment comprises: a handle receiving the proximal end of the push-pull wire; and a wire control member mounted to the handle and engaging the push-pull wire, whereby movement of the wire control member translates the push-pull wire along the longitudinal axis of the push-pull wire.

The handle of an embodiment comprises a push-pull wire guide extending from the handle, and the push-pull wire passes through the push-pull wire guide for transitioning the push-pull wire to the catheter body.

The proximal end of the push-pull wire of an embodiment is attached to a rack bearing a plurality of engagement teeth, and the wire control member engaging the engagement teeth of the rack, whereby movement of the wire control member advances the rack proximally or distally to thereby translate the attached push-pull wire along the longitudinal axis of the push-pull wire.

The wire control member of an embodiment comprises a wheel defining a concentrically configured gear engaging the engagement teeth of the rack, whereby rotation of the wheel advances the rack proximally or distally to thereby translate the push-pull wire along the longitudinal axis of the push-pull wire.

The handle is integrated into a catheter fitting connected to the catheter body, the catheter fitting including a main lumen access and a push-pull wire access.

The proximal end of the push-pull wire of an embodiment is attached to a wire carriage, and the wire control member comprises a carriage screw disposed within the handle, the wire carriage being configured to travel within an advancement channel defined within the handle, and a proximal end of the carriage screw being attached to a control knob that may be rotated to advance the wire carriage and the push-pull wire either proximally or distally along the longitudinal axis of the push-pull wire.

The proximal end of the push-pull wire of an embodiment is attached to a wire carriage, and the handle comprises a control release knob attached to a release screw attached to the wire carriage, whereby the control release knob may be translated proximally or distally such that the wire carriage travels within an advancement channel to advance or retract the push-pull wire.

The control release knob of an embodiment may be tightened about the release screw against the handle to lock a position of the push-pull wire.

The proximal end of the push-pull wire of an embodiment is attached to a wire carriage, and wherein the wire control member comprises a control slide configured to proximally or distally advance the wire carriage within the handle to thereby translate the push-pull wire along the longitudinal axis of the push-pull wire.

Embodiments described herein include a catheter section comprising a catheter body having a proximal end and a distal end. The catheter body includes a distal flexible joint region, a main lumen extending through the catheter body and through the flexible joint region, and a wire lumen adjacent to the main lumen and extending through the catheter body and through the flexible joint region. The wire lumen of the flexible joint region has an opening near or at a distal end of the flexible joint region. Embodiments include a push-pull wire configured to be pushed or pulled along a longitudinal axis of the wire through the wire lumen. The distal end of the push-pull wire is attached to the distal flexible joint region. The push-pull wire has a proximal portion of a first diameter and a distal portion of a smaller diameter than the first diameter. Embodiments include a coil disposed around the smaller diameter distal portion of the push-pull wire. Embodiments include a control in communication with a proximal end of the push-pull wire for manipulating the flexible joint region.

Embodiments described herein include a catheter section comprising: a catheter body having a proximal end and a distal end, the catheter body including a distal flexible joint region, a main lumen extending through the catheter body and through the flexible joint region, and a wire lumen adjacent to the main lumen and extending through the catheter body and through the flexible joint region, the wire lumen of the flexible joint region having an opening near or at a distal end of the flexible joint region; a push-pull wire configured to be pushed or pulled along a longitudinal axis of the wire through the wire lumen, the distal end of the push-pull wire attached to the distal flexible joint region, the push-pull wire having a proximal portion of a first diameter and a distal portion of a smaller diameter than the first diameter; a coil disposed around the smaller diameter distal portion of the push-pull wire; and a control in communication with a proximal end of the push-pull wire for manipulating the flexible joint region.

The catheter section of an embodiment includes a coating of a material with a low coefficient of friction disposed over the push-pull wire.

The catheter section of an embodiment includes a strapping coil disposed around the outside of the catheter.

The catheter section of an embodiment includes an outer covering formed of a polymeric material disposed around the strapping coil.

The outer covering disposed around the strapping coil of an embodiment is formed of PEBAX.

The catheter section of an embodiment includes an outer covering of a mesh formed of a polymeric material disposed around the distal tip of the catheter.

The mesh of an embodiment is formed of polyethylene terephthalate.

The catheter section of an embodiment includes at least one radio-opaque band near or at the distal end of the flexible joint region.

The wire lumen of an embodiment comprises a braid along at least a substantial portion of the wire lumen.

The braid of an embodiment terminates proximally of the flexible joint region. The main lumen of an embodiment comprises a lining along at least a substantial portion of the main lumen.

The lining of an embodiment comprises a lubricious lining.

The wire lumen of an embodiment comprises a lining along at least a substantial portion of the wire lumen.

The lining of an embodiment comprises a lubricious lining.

The push-pull wire of an embodiment extends through the opening of the wire lumen at the distal end of the flexible joint region, and is attached to the marker band.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the device and corresponding systems and methods is not intended to be exhaustive or to limit the systems and methods to the precise forms disclosed. While specific embodiments of, and examples for, the device and corresponding systems and methods are described herein for illustrative purposes, various equivalent modifications are possible within the scope of the systems and methods, as those skilled in the relevant art will recognize. The teachings of the device and corresponding systems and methods provided herein can be applied to other systems and methods, not only for the systems and methods described above.

The elements and acts of the various embodiments described above can be combined to provide further embodiments. These and other changes can be made to the device and corresponding systems and methods in light of the above detailed description.

In general, in the following claims, the terms used should not be construed to limit the device and corresponding systems and methods to the specific embodiments disclosed in the specification and the claims, but should be construed to include all systems that operate under the claims. Accordingly, the device and corresponding systems and methods is not limited by the disclosure, but instead the scope is to be determined entirely by the claims.

While certain aspects of the device and corresponding systems and methods are presented below in certain claim forms, the inventors contemplate the various aspects of the device and corresponding systems and methods in any number of claim forms. Accordingly, the inventors reserve the right to add additional claims after filing the application to pursue such additional claim forms for other aspects of the device and corresponding systems and methods.

What is claimed is:

1. A device comprising:
   a catheter section comprising a distal end, a proximal end, and a flexible region located at the distal end;
   a laser fiber disposed within the catheter section, wherein the laser fiber is configured to emit laser light at a fiber distal end; and
   a wire comprising a distal end coupled to the catheter section, wherein the wire is configured to effect flexion of the distal end of the catheter section about the flexible region, wherein a distal portion of the wire has a smaller diameter than a proximal portion of the wire.

2. The device of claim 1, comprising a first lumen disposed within the catheter section, wherein the first lumen comprises an open distal end at a proximal end of the catheter section, wherein the wire is configured to be pushed and pulled through the first lumen along a longitudinal axis of the wire.

3. The device of claim 2, comprising a second lumen disposed within the catheter section adjacent the first lumen, wherein the laser fiber is deployed via the second lumen.

4. The device of claim 3, comprising a guidewire.

5. The device of claim 4, wherein the guidewire is deployed via the second lumen.

6. The device of claim 4, comprising a guidewire lumen disposed within the catheter section adjacent the first lumen, wherein the guidewire is deployed via the guidewire lumen.

7. The device of claim 4, wherein the guidewire has at least one of a variable stiffness along its length and a stepped diameter along its length.

8. The device of claim 1, comprising a radio-opaque band fixed to the catheter section.

9. The device of claim 8, wherein the distal end of the wire is secured to the radio-opaque band.

10. The device of claim 1, comprising an inflatable member.

11. The device of claim 10, wherein the flexible region is distal of the inflatable member.

12. The device of claim 10, wherein the flexible region is disposed within the inflatable member.

13. The device of claim 10, wherein the flexible region is proximal of the inflatable member.

14. The device of claim 10, wherein the inflatable member comprises at least one of elastomer, thermoplastic polymer, silicone rubber, latex rubber, natural rubber, butadiene-based co-polymer, polyvinyl chloride, complex co-polymer, styrene-ethylene butylene-styrene co-polymer, polyethylene, polypropylene, and Nylon.

15. The device of claim 1, wherein the flexible region comprises a coil member.

16. The device of claim 15, wherein the coil member includes a section comprising a pitch that is larger than adjacent coil pitches.

17. The device of claim 1, wherein the flexible region comprises a braid.

18. The device of claim 17, wherein the braid comprises a section with a pic that is larger than adjacent pics.

19. The device of claim 1, wherein the flexible region comprises a polymer that is more pliable than a polymer in at least one adjacent region of the catheter section.

20. The device of claim 1, wherein the flexible region comprises a wall thickness that is thinner than at least one adjacent wall thickness.

21. A method comprising:
configuring a catheter section to include a distal end, a proximal end, and a flexible region located at the distal end;
configuring the catheter section to include a laser fiber configured to emit laser light at a fiber distal end; and
configuring the catheter section to include a wire comprising a distal end coupled to the catheter section, wherein the wire is configured to effect flexion of the distal end of the catheter section about the flexible region, wherein a distal portion of the wire has a smaller diameter than a proximal portion of the wire.

* * * * *